US009384582B2

(12) United States Patent
Izatt et al.

(10) Patent No.: US 9,384,582 B2
(45) Date of Patent: Jul. 5, 2016

(54) METHODS AND COMPUTER PROGRAM PRODUCTS FOR QUANTITATIVE THREE-DIMENSIONAL IMAGE CORRECTION AND CLINICAL PARAMETER COMPUTATION IN OPTICAL COHERENCE TOMOGRAPHY

(71) Applicant: DUKE UNIVERSITY, Durham, NC (US)

(72) Inventors: Joseph A. Izatt, Raleigh, NC (US); Mingtao Zhao, Durham, NC (US); Anthony N. Kuo, Durham, NC (US)

(73) Assignee: Duke University, Durham, NC (US)

( * ) Notice: Subject to any disclaimer, the term of this patent is extended or adjusted under 35 U.S.C. 154(b) by 100 days.

(21) Appl. No.: 13/999,539

(22) Filed: Mar. 7, 2014

(65) Prior Publication Data
US 2014/0241605 A1 Aug. 28, 2014

Related U.S. Application Data

(63) Continuation of application No. 12/799,890, filed on May 4, 2010, now Pat. No. 8,693,745.

(51) Int. Cl.
| | |
|---|---|
| G06K 9/00 | (2006.01) |
| G06T 15/00 | (2011.01) |
| G01B 11/24 | (2006.01) |
| G01B 9/02 | (2006.01) |
| G06T 5/00 | (2006.01) |

(52) U.S. Cl.
CPC ............ *G06T 15/00* (2013.01); *G01B 9/02083* (2013.01); *G01B 9/02091* (2013.01); *G01B 11/2441* (2013.01); *G06T 5/006* (2013.01); *G06T 2207/10101* (2013.01); *G06T 2207/30041* (2013.01)

(58) Field of Classification Search
None
See application file for complete search history.

(56) References Cited

U.S. PATENT DOCUMENTS

| 4,052,889 A | 10/1977 | Mucciardi et al. |
| 5,491,524 A | 2/1996 | Hellmuth et al. |

(Continued)

FOREIGN PATENT DOCUMENTS

| EP | 2427723 | 3/2012 |
| WO | WO 2010-129544 | 11/2010 |

OTHER PUBLICATIONS

Optical coherence tomography . . . topography, Ortiz et al., Applied Optics, vol. 48, No. 35/Dec 10 2009, pp. 6708-6715.*

(Continued)

*Primary Examiner* — Jayesh A Patel
(74) *Attorney, Agent, or Firm* — Jenkins, Wilson, Taylor & Hunt, P.A.

(57) ABSTRACT

Methods and computer program products for quantitative three-dimensional ("3D") image correction in optical coherence tomography. Using the methods and computer program products, index interface (refracting) surfaces from the raw optical coherence tomography ("OCT") dataset from an OCT system can be segmented. Normal vectors or partial derivatives of the curvature at a refracting surface can be calculated to obtain a refracted image voxel. A new position of each desired refracted image voxel can be iteratively computed. New refracted corrected voxel positions to an even sampling grid can be interpolated to provide corrected image data. In some embodiments, clinical outputs from the corrected image data can be computed.

71 Claims, 8 Drawing Sheets
(6 of 8 Drawing Sheet(s) Filed in Color)

(56) References Cited

U.S. PATENT DOCUMENTS

| | | | |
|---|---|---|---|
| 5,588,435 A | 12/1996 | Weng et al. | |
| 5,994,690 A | 11/1999 | Kulkarni et al. | |
| 6,191,862 B1* | 2/2001 | Swanson | G01B 11/2441 356/479 |
| 6,552,806 B1 | 4/2003 | Swinford et al. | |
| 6,618,152 B2 | 9/2003 | Toida | |
| 6,887,231 B2 | 5/2005 | Mrochen et al. | |
| 6,940,557 B2 | 9/2005 | Handjojo et al. | |
| 7,092,748 B2 | 8/2006 | Valdes Sosa et al. | |
| 7,102,756 B2 | 9/2006 | Izatt et al. | |
| 7,187,800 B2 | 3/2007 | Hibbard | |
| 7,330,270 B2 | 2/2008 | O'Hara et al. | |
| 7,486,406 B2 | 2/2009 | Kim | |
| 7,602,500 B2 | 10/2009 | Izatt | |
| 7,648,242 B2 | 1/2010 | Ferguson et al. | |
| 7,719,692 B2 | 5/2010 | Izatt | |
| 7,796,243 B2 | 9/2010 | Choo-Smith et al. | |
| 7,907,765 B2 | 3/2011 | Fauver et al. | |
| 7,990,541 B2 | 8/2011 | Izatt | |
| 8,098,275 B2* | 1/2012 | Keating, III | H04N 13/0207 345/424 |
| 8,149,418 B2 | 4/2012 | Tearney et al. | |
| 8,155,420 B2 | 4/2012 | Meyer et al. | |
| 8,565,499 B2 | 10/2013 | Zhao et al. | |
| 8,693,745 B2 | 4/2014 | Izatt | |
| 8,718,743 B2 | 5/2014 | Izatt | |
| 2002/0122530 A1* | 9/2002 | Erbel | A61B 6/0421 378/62 |
| 2002/0123680 A1* | 9/2002 | Vaillant | G06T 11/006 600/407 |
| 2005/0057756 A1* | 3/2005 | Fang-Yen | G01B 9/02072 356/497 |
| 2005/0171438 A1 | 8/2005 | Chen et al. | |
| 2007/0258094 A1 | 11/2007 | Izatt et al. | |
| 2008/0140341 A1* | 6/2008 | Ralston | G01N 21/4795 702/155 |
| 2008/0309881 A1 | 12/2008 | Huang et al. | |
| 2009/0131921 A1* | 5/2009 | Kurtz | A61F 9/00825 606/4 |
| 2009/0163796 A1* | 6/2009 | Simpson | A61B 5/0066 600/407 |
| 2009/0185166 A1 | 7/2009 | Oldenburg et al. | |
| 2009/0257636 A1 | 10/2009 | Wei et al. | |
| 2009/0270738 A1 | 10/2009 | Izatt | |
| 2009/0290167 A1 | 11/2009 | Flanders et al. | |
| 2010/0124158 A1 | 5/2010 | Leto | |
| 2010/0150467 A1 | 6/2010 | Zhao | |
| 2010/0309477 A1 | 12/2010 | Yun et al. | |
| 2010/0309480 A1 | 12/2010 | Furusawa | |
| 2011/0007321 A1 | 1/2011 | Everett et al. | |
| 2011/0032533 A1 | 2/2011 | Izatt | |
| 2012/0188555 A1 | 7/2012 | Izatt | |

OTHER PUBLICATIONS 3D refraction—Cornea, Zhao et al., Optics express vol. 18, No. 9, Apr. 26, 2010, pp. 8923-8936.*

O. W. Richards, "Phase Difference Microscopy," Nature, 1944, vol. 154, No. 672.

C. R. Tilford, "Analytical procedure for determining lengths from fractional fringes," Appl. Opt. 16, 1977, pp. 1857-1860.

Y. Cheng and J. C. Wyant, "Two-wavelength phase shifting interferometry," Appl. Opt. 23, 1984, pp. 4539-4543.

K. Creath, "Phase-shifting speckle interferometry," Appl. Opt. 24, 1985, pp. 3053-3058.

H. Gundlach, "Phase contrast and differential interference contrast instrumentation and applications in cell, developmental, and marine biology," Opt. Eng. 32, 1993, pp. 3223-3228.

E. Cuche, F. Bevilacqua, and C. Depeursinge, "Digital Holography for quantitative phase-contrast imaging," Opt. Lett. 24, 1999, pp. 291-293.

C.K. Hitzenberger, M. Sticker, R. Leitgeb, and A.F. Fercher, "Differential phase measurements in low-coherence interferometry without $2\pi$ ambiguity," Opt. Lett. 26, 2001, pp. 1864-1866.

Hitzenberger et al., "Overcoming the 2it ambiguity in low coherence interferometric differential phase measurements," Proc. SPIE, Coherence Domain Optical Methods in Biomedical Science and Clinical Applications, 2001, vol. 4251, pp. 81-85.

C. Yang, A. Wax, R.R. Dasari, and M.S. Feld, "$2\pi$ ambiguity-free optical distance measurement with subnanometer precision with a novel phase-crossing low-coherence interferometer," Opt. Lett. 27, 2002, pp. 77-79.

D.R. Lide, ed., "CRC Handbook of Chemistry and Physics," CRC Press, 2001-2002.

Ding et al., "Real-time phase-resolved optical coherence tomography and optical Doppler tomography." Optics Express, Mar. 2002, vol. 10 No. 5.

R. Tripathi, N. Nassif, J. S. Nelson, B. H. Park, and J. F. De Boer, "Spectral shaping for non-Gaussian source spectra in optical coherence tomography," Opt. Lett. 27, 2002, pp. 406-408.

Westphal, Volker et al., "Correction of Geometric and Refractive Image Distortions in Optical Coherence Tomography Applying Fermat's Principle," Optics Express, May 6, 2002, pp. 397-404, vol. 10, No. 9.

J. Gass, A. Dakoff, and M. K. Kim, "Phase imaging without $2\pi$ ambiguity by multiwavelength digital holography," Opt. Lett. 28, 2003, pp. 1141-1143.

J.F. De Boer, B. Cense, B. H. Park, M. C. Pierce, G. J. Tearney, and B. E. Bouma, "Improved signal-to-noise ratio in spectral-domain compared with time-domain optical coherence tomography," Opt. Lett. 28, 2003, pp. 2067-2069.

M. A. Choma, M. V. Sarunic, C. Yang, and J. A. Izatt, "Sensitivity advantage of swept source and Fourier domain optical coherence tomography," Opt. Express 11, 2003, pp. 2183-2189.

R. Leitgeb, C. K. Hitzenberger, and A. F. Fercher, "Performance of Fourier domain vs. time domain optical coherence tomography," Opt. Express 11, 2003, pp. 889-894.

Zawadzki, Robert J. et al., "Three-Dimensional Ophthalmic Optical Coherence Tomography With a Refraction Correction Algorithm," SPIE, 2003, vol. 5140.

D.L. Marks, P.S. Carney, and S.A. Boppart, "Adaptive spectral apodization for sidelobe reduction in optical coherence tomography images," J. Biomed. Opt. 9, 2004, pp. 1281-1287.

G. Popescu, L. P. DeFlores, J.C. Vaughan, K. Badizadegan, H. Iwai, R. R. Dasari, and M. S. Feld, "Fourier phase microscopy for investigation of biological structures and dynamics," Opt. Lett. 29, 2004, pp. 2503-2505.

Tang, Maolong, "Corneal Mean Curvature Mapping: Applications in Laser Refractive Surgery," Biomedical Engineering Center, 2004, Ohio State University.

Yun, S. et al., "Removing the depth-degeneracy in optical frequency domain imaging with frequency shifting," Optics Express, Oct. 4, 2004, vol. 12, No. 20.

C. Joo, T. Akkin, B. Cense, B. H. Park, and J. F. De Boer, "Spectral-domain optical coherence phase microscopy for quantitative phase-contrast imaging," Opt. Lett. 30, 2005, pp. 2131-2133.

C. J. Mann, L. Yu, C. Lo, and M. K. Kim, "High-resolution quantitative phase-contrast microscopy by digital holography," Opt. Express 13, 2005, pp. 8693-8698.

Davis, A.M. et al., "Heterodyne swept-source optical coherence tomography for complete complex conjugate ambiguity removal," Journal of Biomedical Optics, Nov./Dec. 2005, vol. 10, No. 6.

G. Popescu, T. Ikeda, C. A. Best, K. Badizadegan, R. R. Dasari, and M. S. Feld, "Erythrocyte structure and dynamics quantified by Hilbert phase microscopy," J. Biomed. Opt. 10, 2005, 060503.

M. A. Choma, A. K. Ellerbee, C. Yang, T. L. Creazzo, and J. A. Izatt, "Spectral-domain phase microscopy," Opt. Lett. 30, 2005, pp. 1162-1164.

T. Ikeda, G. Popescu, R. R. Dasari, and M.S. Feld, "Hilbert phase microscopy for investigating fast dynamics in transparent systems," Opt. Lett. 30, 2005, pp. 1165-1167.

M. A. Choma, A. K. Ellerbee, S. Yazsanfar, and J. A. Izatt, "Doppler flow imaging of cytoplasm streaming using spectral domain phase mircoscopy," J. Biomed. Opt. 11, 2006, 024014.

Sicam, Victor Arni D.P., "Spherical Aberration of the Anterior and Posterior Surfaces of the Human Cornea," J. Opt. Soc. Am. A, Mar. 2006, pp. 544-549, vol. 23, No. 3.

(56) References Cited

OTHER PUBLICATIONS

Tang, Maolong et al., "Measuring Total Corneal Power Before and After Laser In Situ Keratomileusis With High-Speed Optical Coherence Tomography," J. Cataract Refract Surg, Nov. 2006, pp. 1843-1850, vol. 32, No. 11.

A. K. Ellerbee and J.A. Izatt, "Phase retrieval in low-coherence interferometric microscopy,"Opt. Lett. 32, 2007, pp. 388-390.

A. K. Ellerbee, T. L. Creazzo, and J. A. Izatt, "Investigating nanoscale cellular dynamics with cross-sectional spectral domain phase microscopy," Opt. Express 15, 2007, pp. 8115-8124.

E. J. McDowell, A. K. Ellerbee, M. A. Choma, B. E. Applegate, and J. A. Izatt, "Spectral domain phase microscopy for local measurements of cytoskeletal rheology in single cells," J. Biomed. Opt., 2007, 04400.

J. Kuhn, T. Colomb, F. Montfort, F. Charrière, Y. Emery, E. Cuche, P. Marquet, and C. Depeursinge, "Real-Time dual-wavelength digital holographic microscopy with a single hologram acquistion," Opt. Express 15, 2007, pp. 7231-7242.

N. Warnasooriya and M.K. Kim, "LED-based multi-wavelength phase imaging interference microscopy," Opt. Express 15, 2007, pp. 9239-9247.

Wang et al., "Three dimensional optical angiography." Optics Express, 2007, pp. 4083-4097, vol. 15 No. 7.

Wang, "Three-dimensional optical micro-angiography maps directional blood perfusion deep within microcirculation tissues beds in vivo," Phys. Med. Biol. 2007, pp. N531-N537, vol. 52.

N. Lue, W. Choi, G. Popescu, T. Ikeda, R. R. Dasari, K. Badizadegan, and M. S. Feld, "Quantitative phase imaging of live cells using fast Fourier phase microscopy," Appl. Oct. 46, 2007, pp. 1836-1842.

A. Khmaladze, A. Restrepro-Martínez, M.K. Kim, R. Castañeda, and A. Blandón, "Simultaneous Dual-Wavelength Reflection Digital Holography Applied to the Study of the Porous Coal Samples," Appl. Opt. 47, 2008, pp. 3203-3210.

D. L. Marks, S.C. Schlachter, A.M. Zysk, and S.A. Boppart, "Group refractive index reconstruction with broadband interferometric confocal microscopy," J. Opt. Soc. Am. A 25, 2008, pp. 1156-1164.

Erich Götzinger, Michael Pircher, Wolfgang Geitzenauer, Christian Ahlers, Bernhard Baumann, Stephan Michels, Ursula Schmidt-Erfurth, and Christoph K. Hitzemberger, "Retinal pigment epithelium segmentation by polarization sensitive optical coherence tomography," Opt. Express, 2008, pp. 16410-16422.

J.A. Izatt and M.A. Choma, "Theory of Optical Coherence Tomography," in Optical Coherence Tomography: Technology and Applications, W. Drexler and J.G. Fujimoto, eds, Springer, 2008.

R. M. Werkmeister, N. Dragostinoff, M. Pircher, E. Götzinger, C. K. Hitzenberger, R. A. Leitgeb, and L. Schmetterer, "Bidirectional Doppler Fourier-domain optical coherence tomography for measurement of absolute flow velocities in human retinal vessels," Opt. Lett. 33, 2008, pp. 2967-2969.

S. Tamano et al., "Phase-shifting digital holography with a low-coherence light source for reconstruction of a digital relief object hidden behind a light-scattering medium," Applied Optics, 2008, pp. 953-959, vol. 45, No. 5, Optical Society of America.

Sarunic, Marinko et al., "Imaging the Ocular Anterior Segment With Real-Time, Full-Range Fourier-Domain Optical Coherence Tomography,"Arch. Opthal., Apr. 2008, pp. 537-542, vol. 126, No. 4.

Vergnole et al., "Common Path swept source OCT interferometer with artifact removal." Proc of SPIE, 2008, 8 pages, vol. 6847.

V. Srinivasan, B.K. Monson, M. Wojtkowski, R.A. Bilonick, I. Gorczynksa, R. Chen, J.S. Duker, J.S. Schumann, J.G. Fujimoto, "Characterization of Outer Retinal Morphology with High-Speed, Ultrahigh Resolution Optical Coherence Tomography," Investigative Ophthalmology and Visual Science 49, 2008, pp. 1571-1579.

H. C. Hendargo, M. Zhao, N. Shepard, and J.A. Izatt, "Synthetic wavelength based phase unwrapping in spectral domain optical coherence tomography," Opt. Express 17, 2009, pp. 5039-5051.

Hendargo et al., "Synthetic Wavelength-Based Phase Unwrapping in Fourier Domain Optical Coherence Tomography," Optics Express, 2009, pp. 5039-5051, vol. 17, Issue 7. http://dx.doi.org/10.1364/OE.17.005039.

Jae Ho Han et al., "Common path fourier domain optical coherence tomography in ophthalmology applications," Life Science Systems and Applications Workshop, 2009, pp. 163-166.

Zhao, Mingtao et al., "Single-Camera Sequential-Scan-Based Polarization-Sensitive SDOCT for Retinal Imaging," Optics Letters, Jan. 15, 2009, pp. 205-207, vol. 34, No. 2.

Liu et al., "Compressive SD-OCT: the application of compressed sensing in spectral domain optical coherence tomography," Optics Express, 2010, pp. 22010-22019, vol. 18, Issue 21.

Wieserlabs UG Data Sheet—1 GHz Dual-Balanced InGaAs Low Noise Photodetector No. WL-BPD1GA, www.wieserlabs.com, Oct. 2011.

Yogesh, Verma et al., "Use of common path phase sensitive spectral domain optical coherence tomography for refractive index measurements." Applied Optics, 2011, pp. E7-E12, vol. 50, Issue 25.

Park et al., "Double common-path interferometer for flexible optical probe of optical coherence tomography," Optics Express, 2012, pp. 1102-1112, vol. 20, Issue 2.

Uhlhorn et al., "Refractive Index Measurement of the Isolated Crystalline Lens Using Optical Coherence Tomography,"Vision Research 48 (2008), pp. 2732-2738.

International Search Report and Written Opinion for Application No. PCT/US2010/033540 dated Jul. 16, 2010.

Non-Final Office Action for U.S. Appl. No. 12/386,945 dated Jul. 13, 2011.

Final Office Action for U.S. Appl. No. 12/386,945 dated May 23, 2012.

Non-Final Office Action for U.S. Appl. No. 12/460,532 dated Jul. 13, 2012.

Notice of Allowance for U.S. Appl. No. 12/460,532 dated Feb. 20, 2013.

Non-Final Office Action for U.S. Appl. No. 12/386,945 dated Mar. 19, 2013.

Notice of Allowance for U.S. Appl. No. 12/460,532 dated May 24, 2013.

Non-Final Office Action for U.S. Appl. No. 12/799,890 dated Aug. 9, 2013.

Notice of Allowance for U.S. Appl. No. 12/799,890 dated Nov. 19, 2013.

Notice of Allowance for U.S. Appl. No. 12/386,945 dated Jan. 29, 2014.

Restriction Requirement for U.S. Appl. No. 13/355,381 dated Feb. 13, 2014.

Non-Final Office Action for U.S. Appl. No. 13/355,381 dated Aug. 12, 2014.

Final Office Action for U.S. Appl. No. 13/355,381 dated May 15, 2015.

Advisory Action for U.S. Appl. No. 13/355,381 dated Sep. 29, 2015.

Notice of Allowance for U.S. Appl. No. 13/355,381 dated Nov. 4, 2015.

* cited by examiner

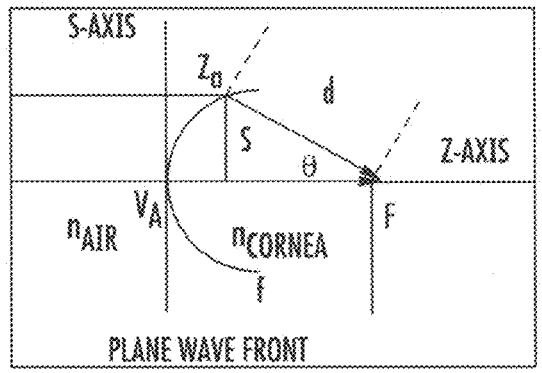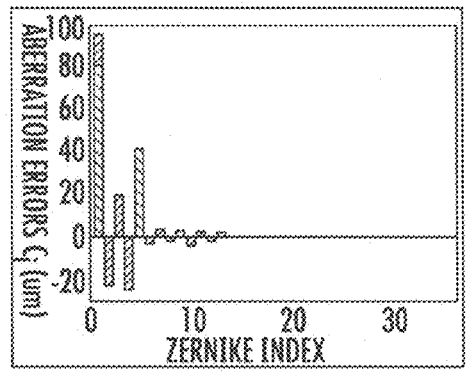
FIG. 13A  FIG. 13B
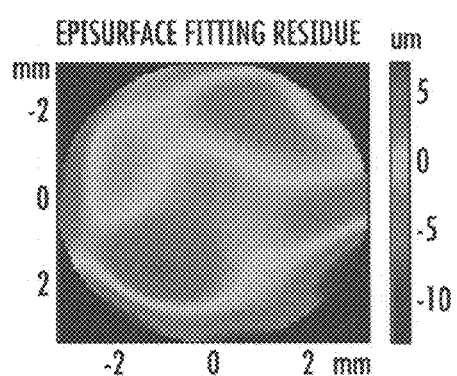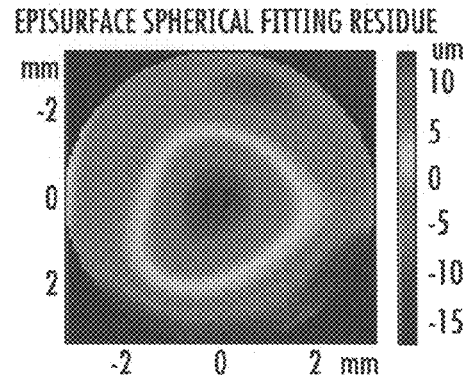
FIG. 14A  FIG. 14B
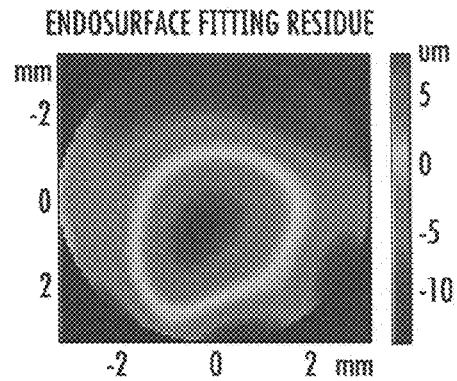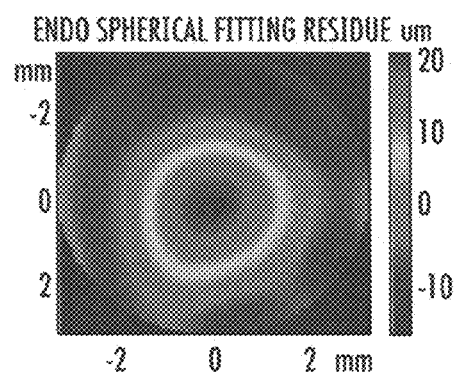
FIG. 14C  FIG. 14D

METHODS AND COMPUTER PROGRAM PRODUCTS FOR QUANTITATIVE THREE-DIMENSIONAL IMAGE CORRECTION AND CLINICAL PARAMETER COMPUTATION IN OPTICAL COHERENCE TOMOGRAPHY

RELATED APPLICATION

The presently disclosed subject matter is a continuation of U.S. patent application Ser. No. 12/799,890, filed May 4, 2010, the disclosure of which is incorporated herein by reference in its entirety.

GOVERNMENT INTEREST

This invention was made with government support under Grant Nos. R21 EY017393 and K12-EY01633305 awarded by the National Institutes of Health. The government has certain rights in the invention.

TECHNICAL FIELD

The present subject matter generally relates to optical coherence tomography ("OCT"). More particularly, the present subject matter relates to OCT for use in analysis of ocular optical elements and surfaces, such as the cornea and lens of the eye.

BACKGROUND

Multiple modalities currently exist to image the ocular anterior segment of an eye. These imaging devices aid in the clinical diagnosis and care of ocular disease. Optical coherence tomography ("OCT") is one such technique used to image in vivo the ocular anterior segment of an eye in a non-invasive fashion. Specific implementations can comprise time-domain OCT systems (such as those sold under the name of VISANTE® by Carl Zeiss Meditec, Inc.), and Fourier-domain OCT systems, including both swept-source and spectrometer-based spectral-domain ("SDOCT") implementations. Many previously disclosed anterior segment OCT systems have utilized illumination light in the 1310 nm region. Recently, several SD-OCT systems have been developed that utilize an 840 nm light source and are designed for imaging the retina, but that can also be modified with an adapter or a separate patient interface to image the ocular anterior segment of an eye. These SD-OCT systems offer the advantage of higher axial resolutions and faster scanning over prior systems.

All OCT imaging systems are subject to the effects of refraction at surfaces corresponding to interfaces between regions of differing refractive index within a sample, including between the air and the surface of the sample as well as internal sample interface surfaces. For a sample such as the anterior segment of an eye, important refractive index interfaces comprise the outer, herein referred to as epithelial, and inner, herein referred to as endothelial surfaces of the cornea, as well as the outer and inner surfaces of the crystalline lens. Additionally, for samples containing regions of different refractive index, it can be important for images acquired of the sample to reflect the true physical dimensions of the sample rather than to be distorted by the varying speed of light in different sample regions. Both of these potential pitfalls can be particularly important in applications such as corneal biometry where accurate measurements of various clinically significant parameters must be computed from the image data. Such computations are very sensitive to even small image errors due to refraction or distortion. Most current OCT systems do not correct the raw image data for refraction at sample interfaces or for the effects of different sample regions having differing refractive indices. Most current OCT systems instead assume that the light incident on the sample continues in a straight line through the sample and thus plot the raw image A-scan data corresponding to a depth-resolved reflectivity map of the sample on this assumed undeviated path. These systems also do not correct for the effects of different refractive indices in different regions of the sample. At best, these systems may divide the observed A-scan data by some assumed average index of refraction of the entire sample. As such, raw OCT data in current generation OCT systems does not accurately represent the true position of internal sample structures and are thus not able to support calculation of clinically significant parameters which depend on accurate image data. In particular, to produce accurate quantitative measurements of structures of the ocular anterior segment, accounting for the effects of refraction of the sample arm light and for the effects of differing indices of refraction in different sample regions is required.

Prior methods to correct for refraction in OCT images have been developed. They do not, however, account accurately or completely for correction of volumetric, three-dimensional ("3D") OCT datasets. One method is limited to two-dimensional ("2D") processing, which assumes that refraction occurs only within the plane of individual acquired B-scans (defined as sets of A-scans acquired along a straight line comprising a cross-sectional image of the sample). For a curved 3D structure such as the cornea, 2D refraction correction is correct only if the sample is rotationally conically symmetric about some axis passing through the apex of the sample, and if the acquired B-scan data passed exactly through the apex point. The first condition is rarely true for realistic samples such as the human cornea, especially if they have been modified surgically. The second condition is true only for idealized radial scan patterns, which may not be optimal because they oversample the central region and undersample the outer region and in any case are difficult to obtain correctly due to unavoidable patient motion or operator misalignment of the OCT system.

SUMMARY

In accordance with this disclosure, methods and tools for providing quantitative three-dimensional ("3D") image correcting clinical parameter computations for optical coherence tomography are provided. It is, therefore, an object of the present disclosure to provide 3D imaging correction tools that can be used with any optical or ultrasonic imaging tools when curved surfaces are presented along the imaging path. Another object of the present disclosure is to provide methods for improving the 3D imaging of the eye to more accurately portray the refracting surfaces of the eye for diagnosis and treatment purposes.

This and other objects of the present disclosure as can become apparent from the present disclosure are achieved, at least in whole or in part, by the subject matter described herein.

BRIEF DESCRIPTION OF THE DRAWINGS

The patent or application file contains at least one drawing executed in color. Copies of this patent or application with color drawing(s) will be provided by the Patent and Trademark Office upon request and payment of necessary fee.

A full and enabling disclosure of the present subject matter including the best mode thereof to one of ordinary skill in the art is set forth more particularly in the remainder of the specification, including reference to the accompanying figures, in which:

FIG. 13A illustrates a diagrammatic representation of wavefront aberration analysis according to the present subject matter;

FIG. 13B illustrates the results of wavefront aberration analysis using Zernike spectrum analysis and ray tracing according to the present subject matter;

FIG. 14A illustrates a float image (difference map of imaged surface against a reference surface) of the anterior surface of a contact lens with asphericity fitting according to the present subject matter;

FIG. 14B illustrates a float image of the posterior surface of a contact lens with best sphere fitting according to the present subject matter;

FIG. 14C illustrates a float image of the posterior surface of a contact lens with asphericity fitting according to the present subject matter; and FIG. 14D illustrates a float image of the posterior surface of a contact lens with best sphere fitting according to the present subject matter

DETAILED DESCRIPTION

Figure 1:
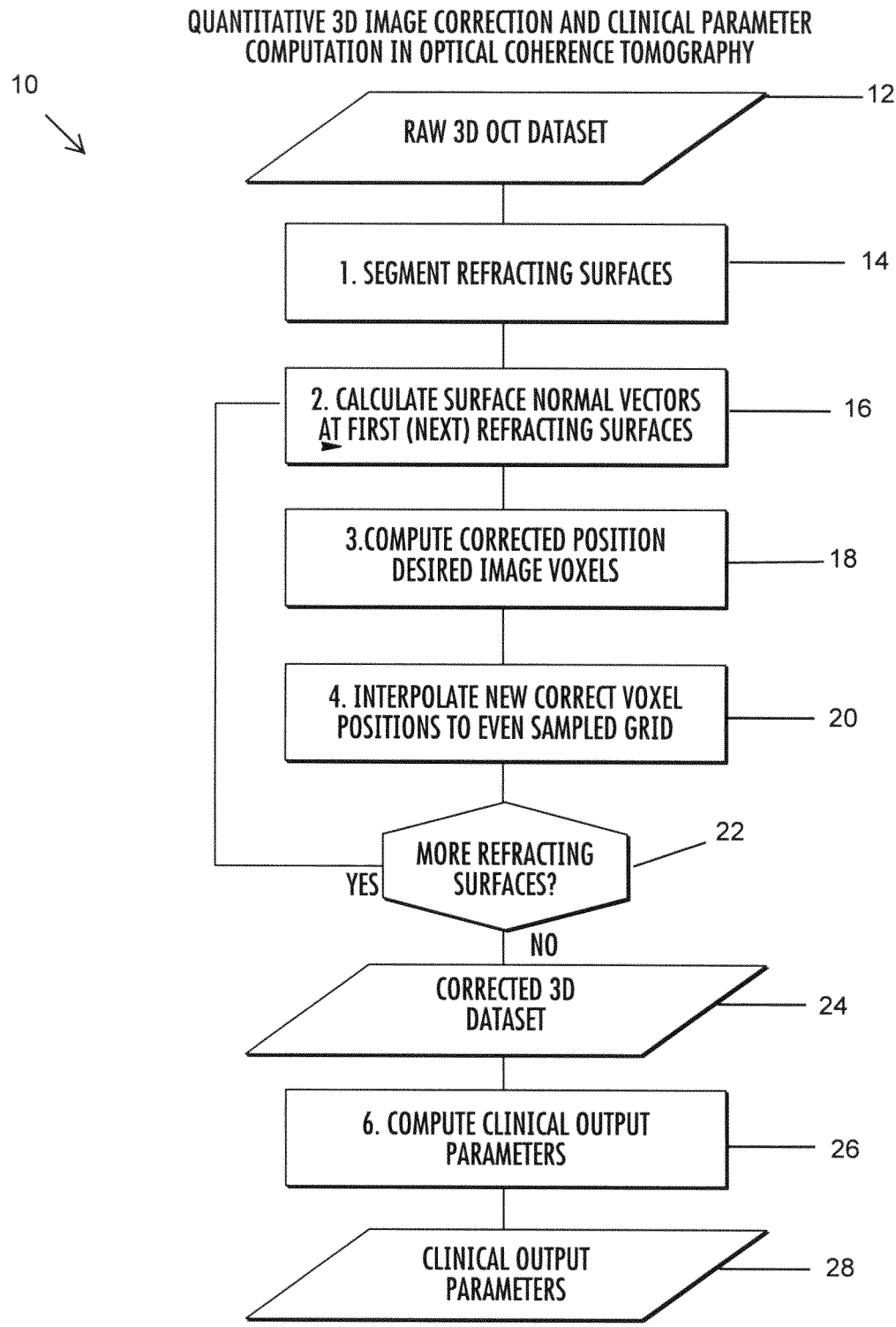
FIG. 1 illustrates a flowchart of an embodiment of a method for correction of refraction and index variations at one or more index interfaces in OCT images according to the present subject matter.

Reference will now be made in detail to possible embodiments of the present subject matter, one or more examples of which are shown in the figures. Each example is provided to explain the subject matter and not as a limitation. In fact, features illustrated or described as part of one embodiment can be used in another embodiment to yield still a further embodiment. It is intended that the subject matter disclosed and envisioned herein covers such modifications and variations.

For meaningful analysis of the cornea of an eye from spectral domain optical coherence tomography ("SD-OCT") data, effects of refraction at the epithelial and endothelial surfaces should be accounted for. A method for three-dimensional ("3D") refraction correction based on a vector representation which accounts for refraction of optical coherence tomography ("OCT") light in the cornea is present herein below. This method can be used to dewarp raw SD-OCT volumes. The method can also be used to reconstruct the true position of the corneal endothelial surface.

In addition, the raw volumetric image dataset may require correction of image artifacts or interpolation of non-sampled or under-sampled areas of the sample prior to further processing. Image artifacts can be caused by mis-calibrations or non-linearities of the image acquisition hardware as well as patient-induced artifacts such as axial or lateral patient motion, loss of patient fixation, or patient blinking during data acquisition.

Following 3D refraction correction of volumetric corneal datasets, an estimate of the corneal thickness and the individual wavefront aberrations of the epithelial and the refraction-corrected endothelial surfaces can be made. To measure the corneal thickness along the episurface normal vector, a numerical method or solution called recursive half searching algorithm ("RHSA") can be used to compute the corneal thickness with fine convergence. The different wavefront aberrations of the anterior and posterior surfaces can be retrieved using Zernike spectrum analysis. To enhance the scattering OCT signal at wide scanning range, the illumination light can be customized to a special polarization state to increase the scattering sensitivity. P polarization states are suggested to improve the imaging depth and reduce the corneal surface scattering. Different scanning patterns can also be explored to optimize the OCT image quality and reduce bulk motion. Asphericity and best spherical fitting can be utilized to retrieve the corneal asphericity, curvature and flow image of both surfaces of ocular anterior segment, which is very useful for clinical applications. The 3D refraction correction algorithms can be used with any optical or ultrasonic imaging tools when some curved surfaces are presented along the imaging path.

Thus, a method is provided for three-dimensional ("3D") correction of refraction and index variations within arbitrary samples. The method can be particularly useful for correction of human ocular anterior segment images obtained in vivo using SDOCT systems including extraction of quantitative clinical parameters from 3D OCT datasets acquired in the cornea. A mathematical model and analytical equations for correction of refraction and index variations can also be provided. Though this method has been reduced to practice for correcting OCT images of the ocular anterior segment and cornea, it can be applied generally to the correction of all imaging modalities whereby the source radiation encounters an interface and structure which alters its path (refraction of electromagnetic or sound waves).

Following correction of refraction and index variations, the corrected data can then be used to generate multiple quantitative clinically significant displays. These can comprise corneal thickness mapping, corneal surface curvature mapping, corneal surface deviation from best fit sphere (float) mapping, corneal-iris angle mapping, and surface wave front aberration analysis among others. Without 3D refraction correction of the raw anatomic images, it would not be possible to generate accurate (and hence clinically useful) versions of these data maps. These displays may be useful for evaluation of pathologies of the cornea or anterior segment, or planning of surgeries such as refractive surgery (e.g. LASIK) or intraocular lens surgery.

The subject matter described herein for quantitative 3D image correction and clinical parameter computation in optical coherence tomography can be implemented using a computer readable medium having stored thereon executable instructions that when executed by the processor of a computer control the processor to perform steps. Exemplary computer readable media suitable for implementing the subject matter described herein includes disk memory devices, programmable logic devices, and application specific integrated circuits. In one implementation, the computer readable medium may comprise a memory accessible by a processor. The memory may comprise instructions executable by the processor for implementing any of the methods for quantitative 3D image correction and clinical parameter computation in optical coherence tomography described herein. In addition, a computer readable medium that implements the subject matter described herein may be distributed across multiple physical devices and/or computing platforms.

The following provides a description for correction of refraction and index variations at one or more index interfaces in OCT images by application of Snell's law generalized to three-dimensions. FIG. 1 illustrates a flowchart of an algorithm, generally designated 10, used for correction of refraction and index variations at one or more index interfaces in OCT images. To begin, a raw OCT dataset 12 can be provided. A step 14 in the method 10 can comprise segmentation of index interface (refracting) surfaces from the raw OCT dataset 12. First, the external and internal sample surfaces at which refraction occurs can be identified. For anterior segment imaging, these correspond to the anterior and posterior surfaces of the cornea and optionally of the crystalline lens. Additionally, the locations within the sample at which it is desired to correct the raw OCT image data for refraction and index variations is identified. These locations can correspond to all positions below the first refracting surface or between all segmented refracting surfaces, or alternatively to only selected sample positions at which it is known a priori that corrected data must be obtained in order to calculate important derived clinical parameters.

For the case of anterior segment imaging, correction of refraction and index variations for all image voxels, or volumetric pixels, can generate a complete de-warped 3D image suitable for viewing and analysis with 3D visualization software tools such as those used in common practice in radiology for analysis of image data from computed tomography (CT) or magnetic resonance (MR) imaging. Alternatively, for anterior segment imaging, correction of refraction and index variations can be limited to structures such as the location of the endothelial surface of the cornea if all that is needed is computation of parameters related solely to the anterior and posterior corneal surfaces such as the corneal thickness, corneal curvature, and corneal wavefront aberrations.

Methods for segmentation of the refracting surfaces can comprise manual techniques requiring human interaction such as marking several points on the refracting surface followed by fitting of a polynomial or other smooth function to the user-generated points. Various methods and software algorithms for automatic segmentation of tissue internal structures can also be used for segmenting of the refracting surfaces, including methods utilizing operations and/or mathematical techniques such as data thresholding, and use of image gradients, snakes, and graph cuts. Thus, in the first step, a raw OCT dataset 12 comprising image brightness as a function of x, y, and z coordinates can be generated/received, and a segmented image dataset of the refractive index interface surfaces comprising sets of the x, y, and z coordinates of the interface surface can be produced.

Another step 16 of the method and method 10 can be to calculate normal vectors or partial derivatives of the curvature at a first refracting surface (or next refracting surface if iterating). To apply Snell's law in 3D using the theoretical model disclosed herein, the normal vector at each point on the segmented refracting surface where the OCT sample arm light strikes the sample can be calculated. If this is the first iteration through the method or refraction, correction is only needed at the first refracting surface, then this step can be applied to the first refracting surface (i.e. for anterior segment imaging, the epithelial corneal surface). If this has already been done for the first refracting surface, then it can be done for the next refracting surface.

The method for calculating the surface normal can depend upon the scan pattern utilized to obtain the raw 3D OCT dataset and upon the coordinate system desired for conducting further computations. In the following examples, a Cartesian coordinate system is used, although the present subject matter can be generalized to any other coordinate system such as a polar coordinate system. For computations using the Cartesian coordinate system, the partial derivatives of the surface curvature in the x and y directions are needed as they relate to the surface normal, which can be calculated either from the surface normals or directly. If the data was acquired using a raster scan pattern oriented in the x or y direction, these derivatives can conveniently be calculated from one-dimensional polynomial functions fit using the well-known least-squares fitting method and algorithm to each raster line in both orthogonal directions. Alternatively, if the data was obtained using any other non-raster scan pattern such as a radial scan pattern, the surface points can first be fit to a 3D Zernike polynomial model following which the surface derivatives at every point may subsequently be calculated analytically or computationally.

Thus, in step 16, a segmented image dataset of the refractive index interface surfaces comprising sets of the x, y, and z coordinates of the interface surface can be generated/received, and a set of surface normal vectors or partial derivatives of the curvature of a refractive surface can be produced. The refracting surface from which the normal vectors or partial derivatives of its respective curvature are derived can be a first refractive surface, or subsequent refractive surfaces, if an iteration is being performed.

After the step 16 of calculating normal vectors or partial derivatives of the curvature at a refracting surface, the method can comprise a step 18 of iteratively computing the new position of each desired refracted image voxel, or volumetric pixel. With knowledge of the direction vector of the incident light at each position on the refracting surface and also of the surface normal at each point, the new corrected position of every desired image voxel beneath that surface (down to the level of the next refracting surface, if there is one) can be computed. For example, the new corrected position of each desired image voxel beneath that surface can be computed using Equations (10) disclosed hereinbelow. The direction vector of the incident light at each position can be known from either a) for the first refracting surface, the direction from which the sample arm light is incident on each position of this first refracting surface, which is a property of the OCT system which must be well known and characterized, or b) for subsequent refracting surfaces, the direction at which the light was refracted from the previous refracting surface.

The equations defined for this step can correct for both the effects of refraction at the sample interface and also for the new index of refraction of the medium following the interface. Thus, in step 18, a raw OCT dataset comprising image brightness as a function of x, y, and z coordinates, a segmented image dataset of the refractive index interface surfaces comprising sets of the x, y, and z coordinates of the interface surface, a set of surface normal vectors or partial derivatives of the curvature of the first (next if iterating) refractive surface, and a set of incident light direction vectors can be generated/received, and a set of corrected x, y, and z coordinates of the new corrected position of each desired image voxel beneath that surface can be produced.

After step 18 of iteratively computing the new position of each desired refracted image voxel, the method can comprise step 20 of interpolating new refracted corrected voxel positions to an even sampling grid. The computation of the new position of each refracted image voxel of the previous step 18 can result in new position locations not located on the original raw image data sampled grid and may thus be difficult to store and to use in making further computations. To correct this, the refraction-corrected voxel reflectivity data can be re-sampled back to the original Cartesian sampling grid. This re-sampling can be accomplished using a number of well known re-sampling algorithms, including Gaussian curves, 3D Zernike curves and wavelets. In one embodiment, step 20 can be performed by fitting the corrected voxel data to a 3D Zernike polynomial model, which can then be re-sampled at any desired grid locations. Thus, in the step 20, a set of corrected x, y, and z coordinates of the new corrected position of every desired image voxel beneath that surface can be generated/received, and a set of interpolated corrected image brightness values as a function of x, y, and z coordinates of an even sampling grid can be produced.

In step 22, it can be determined whether more refracting surfaces are needed. If so, the respective steps 16, 18, 20 of the method of calculating normal vectors or partial derivatives of the curvature at the first (or next if iterating) refracting surface, iteratively computing the new position of each desired refracted image voxel, and interpolation of new refracted corrected voxel positions to an even sampling grid can be repeated until all desired refracting surfaces have been evaluated enabling computation and resampling of all desired image voxels. If no more refracting surfaces are needed, then, at this point, a correct 3D dataset 24 can be considered to have been provided.

The next step 26 in the method 10 can comprise computing clinical outputs from corrected image data. From the three-dimensional refraction and index variation corrected voxels and surfaces, various clinical outputs can then be computed. Thus, in this step 26, a set of interpolated corrected image brightness values as a function of x, y, and z coordinates of an even sampling grid can be generated/received, and a set of clinical output measures, or parameters, 28 comprising numerical values, tables, graphs, images, and maps can be produced.

The method and algorithms described above are provided in more detail below.

Detailed Theory and Methods

In this section, the theoretical and computational details that can be used for implementation of the general method described in the previous section are provided. The example application used for illustration of the method is a quantitative image correction and clinical parameter computation for OCT analysis of the human cornea and anterior chamber, although it should be understood that the same inventive steps and procedures can be applied to many other biological and industrial sample types.

The sample data and images used in this section to illustrate reduction to practice of the present subject matter were acquired using one of two Fourier-domain OCT systems. The first system is a research prototype swept-source OCT system operating at 1310 nm wavelength. The second system is a commercial high-speed SDOCT system operating at 840 nm with a corneal adapter manufactured by Bioptigen, Inc., of Durham, N.C. The commercial system can collect repeated A-scans from a 2048 pixel line scan camera at a readout rate of to 17 kHz. Imaging speed is not a limitation factor for any of the methods described. The axial resolution can be approximately 5 micrometers. For comparison, this is 10-fold greater than the 50 micrometer resolution of a rotating Scheimpflug photography system currently in clinical usage.

The goal of the system is a mathematical model of the human cornea and to use this system to generate equations that can accurately reposition refracted pixels in an ocular anterior segment volumetric dataset.

1. Refraction Correction Theory and Algorithm

One method can be to merely use 2D refraction correction via the well known Snell's law. However, such a method requires an assumption that the corneal surface is rotationally conically symmetric which can be mathematically expressed as:

$$z = z_0 + \frac{1/R \times ((x-x_0)^2 + (y-y_0)^2)}{1 + \sqrt{1 + K((x-x_0)^2 + (y-y_0)^2)/R^2}} \quad (1)$$

In the above expression, $(x_0,y_0,z_0)$ represents the vertex of the rotational conic; $(x,y,z)$ is any point on the rotational conic; R is the apex radius of curvature of the surface; K is the conic parameter which represents the asphericity of a surface. K=1 for a sphere and K=0 for a parabolic surface.

If this equation were true for the corneal surface, the cornea would be exactly rotationally symmetric, and 2D refraction correction would be sufficient by carefully scanning each B-scan exactly through the axis of rotation (apex). Unfortunately for clinical application, the cornea is generally not exactly rotationally symmetric. Therefore, the above assumption cannot be used. This is especially the case in pathologic corneas with gross asymmetry and in surgically altered corneas (LASIK, corneal transplantation), and these corneas are the ones that can benefit most from quantitative imaging.

To reflect physical reality, a general 3D vector implementation of Snell's law can be applied to correct for refraction of any surface shape. The epithelium of the cornea can be mathematically implicitly described as $z_{EPI} - f(x,y) = 0$. In the equation, the function $f(x, y)$ can be expressed in terms of numerical partial derivatives of the measured epithelium.

The derivation of Snell's law for use in three-dimensional applications can be done via Maxwell's equations or more intuitively. In the Maxwell's equations approach, the SDOCT instrument can be designed to telecentrically illuminate the cornea within an fixed diameter area centered on the apex of the cornea, thus constraining the incident light direction across any scan pattern to the +z direction. In any realistic biological or industrial sample, the magnetic current densities $\vec{M}$ are zero. The $\vec{n}$ can be the unit surface normal vector of an arbitrary incident point C on the epithelium surface. According to Maxwell's equations, the electric magnetic field boundary condition can be represented:

$$\vec{n} \times (\vec{E}_{in} - \vec{E}_{ref}) = \vec{M} = 0 \quad (2)$$

Here $\vec{E}_{in}$ and $\vec{E}_{ref}$ are the incident and refracted electric fields individually. The above equation indicates that the incident and refracted electric fields can be continuous on the tangential surface of the incident epithelium interface. In other words, the refracted light still propagates within the same incident plane and only bends in that plane. This is true for both p- and s-polarized incident light. In this regard, it can be useful to point out that Brewster's angle for the cornea is Arc tan$(n_c/n_{air}) \approx 54°$, where $n_c$ is the refractive index of cornea (1.385) and $n_{air}$ is the refractive index of air (1.0). When the diameter of the scanning range is bigger than about 6 mm, the majority of the incident light can be obliquely reflected by the epithelial surface and thus lost if the incident polarization state is random. Thus, OCT images of the cornea in that region can be very weak. However, the incident angle can be quite close to Brewster's angle when the scanning range is bigger than 8 mm. As a result, part of the s-polarized light perpendicular to the incident plane will generally be reflected, but all the p-polarized light within the incident plane will generally be transmitted with no loss. To enhance brightness of OCT images of the cornea for large scan widths, p-polarized light can be thus desirable although the cornea has strong birefringence effects which will change the polarization states of the transmitted p-polarization light into elliptical states.

Figure 2:
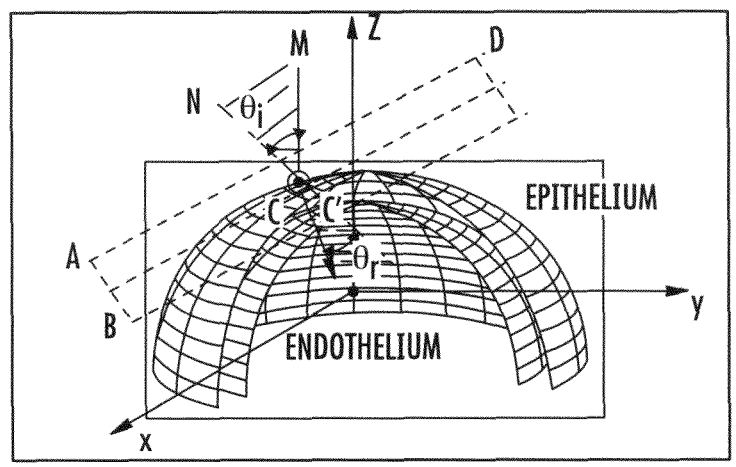
FIG. 2 illustrates an embodiment of a three-dimensional graph on a Cartesian coordinate system of Snell's law for ocular anterior segment OCT imaging according to the present subject matter.

FIG. 2 illustrates a 3D version of Snell's law for ocular anterior segment OCT imaging. In the graphed version, the following variables are provided:

$C(x_0,y_0,z_0)$: Incident point on the epithelium;
$C'(x,y,z)$: intersection point of refraction light with beneath corneal layer,
$\vec{MC}$: incident telecentric light;
$\vec{CC'}$: refraction light;
$\vec{CN} \propto \vec{n}$: surface normal at point C;
$\theta_i$: incident angle; and
$\theta_r$: refraction angle.

As illustrated in FIG. 2, the unit normal vector on the epithelial corneal surface at point C can be expressed as:

$$\vec{n} = \vec{CN}/|\vec{CN}| = \frac{\left(-\frac{\partial z_{EPI}}{\partial x}, -\frac{\partial z_{EPI}}{\partial y}, 1\right)}{\sqrt{\left(\frac{\partial z_{EPI}}{\partial x}\right)^2 + \left(\frac{\partial z_{EPI}}{\partial y}\right)^2 + 1}} \quad (3)$$

The incident light $\vec{MC}$ has direction vector (a,b,c), and the unit vector of the refracted ray $\vec{CC'}$ is:

$$\vec{CC'} = (x-x_0, y-y_0, z-z_0)/\sqrt{(x-x_0)^2+(y-y_0)^2+(z-z_0)^2}. \quad (4)$$

Now $(z-z_0)$ can be obtained using directional vector projection and it is:

$$(z-z_0) = \sqrt{(x-x_0)^2 + (y-y_0)^2 + (z-z_0)^2} \cdot \cos(\theta_{in} - \theta_r) \quad (5)$$
$$= OPL/n_c \cdot \cos(\theta_{in} - \theta_r)$$

In Eq. (5), $\sqrt{(x-x_0)^2+(y-y_0)^2+(z-z_0)^2}$ can be directly retrieved from the optical path length ("OPL") as the distance from the refracting surface to the desired (x,y,z) image voxel in the raw OCT B-scan image. If the Eq. (2) is satisfied, the relationship between the incident light and the refracted light can be represented by the following 3D generalization of Snell's law:

$$\vec{MC} \times (-\vec{n}) \cdot n_{air} = \vec{CC'} \times (-\vec{n}) \cdot n_c. \quad (6)$$

Here × represents the vector cross product. In actual implementation in a Cartesian coordinate system, equation (6) actually can consist of three separate equations, one for each Cartesian axis.

For a more intuitive derivation of Eq. (6), Snell's law serves as the starting point which describes the relationship between an incident ray of light and its refracted ray after encountering a refracting surface (in this case, the cornea):

$$n_{air} * \sin \theta_{incident} = n_{cornea} * \sin \theta_{refracted}. \quad (7)$$

Here, $n_{air}$ is the refractive index of air; $\theta_{incident}$ is the angle between the incident ray of light and the surface normal; $n_{cornea}$ is the refractive index of the cornea; and $\theta_{refracted}$ is the angle between the refracted ray of light and the continuation of the surface normal through the cornea.

The refraction occurs within the same plane. That is, the incident ray and the surface normal (the "incident plane") exist in the same plane as the refracted ray and the surface normal (the "refracted plane"). The problem with OCT is that this particular plane may not be shared with the plane of the B-scan as is normally assumed with prior 2D refraction correction methods. Because the "incident plane" and "refracted plane" share the same larger plane, they also share the same normal vector to this larger plane, particularly at the point of refraction. This shared normal vector passing through the point of refraction can be termed as N. Both sides of Snell's law can be multiplied by this shared normal vector:

$$n_{air} * \sin\theta_{incident} * \vec{N} = n_{cornea} * \sin\theta_{refracted} * \vec{N}. \quad (8)$$

By definition, for a vector $\vec{a}$ and another vector $\vec{b}$, the cross product is $\vec{a} \times \vec{b} = |\vec{a}||\vec{b}|\sin[\theta_{1ab}]=\vec{N}$ where $|\vec{N}|$ is the magnitude of vector $\vec{a}$ and $|\vec{b}|$ is the magnitude of vector $\vec{b}$; $\theta_{ab}$ is the angle between the two vectors; and $\vec{N}$ is the vector normal to the plane created by the two vectors. If the two vectors are unit vectors (each of magnitude 1), then the cross product of two vectors is simply the product of the sine of the angle between the two vectors times the normal to the two vectors. Substituting this definition into equation (8), a vector 3D form of Snell's law is created:

$$n_{air} * \overrightarrow{in \times (nl)} = n_{cornea} * (\overrightarrow{ref} \times \overrightarrow{nl}). \quad (9)$$

Where $\overrightarrow{in}$ is the unit vector describing the incident ray; $\overrightarrow{ref}$ is the unit vector describing the refracted ray; and $\overrightarrow{nl}$ is the surface normal to the cornea for that particular incident ray. This is the same as equation (6) (where $\overrightarrow{MC}$ is an alternative designation for $\overrightarrow{in}$ and $\overrightarrow{cc}$ is an alternative designation for $\overrightarrow{ref}$).

Conversion of each vector to its Cartesian (x, y, z) form and solving the cross product in equation (6) assuming $n_{air}=1.0$ gives the following equations for the refraction corrected positions in the x and y axes (z is given in equation (5) as derived by projection):

$$\begin{cases} z - z_0 = OPL/n_c \cdot \cos(\theta_{in} - \theta_r) \\ x = \dfrac{a * OPL}{n_c^2} + x_0 + \dfrac{\partial z_{EPI}}{\partial x}(c * OPL/n_c^2 - z + z_0) \\ y = \dfrac{b * OPL}{n_c^2} + y_0 + \dfrac{\partial z_{EPI}}{\partial y}(c * OPL/n_c^2 - z + z_0) \end{cases} \quad (10)$$

If the incident light is telecentrically scanned, then incident light vector $\overrightarrow{MC}$ becomes (0,0,-1) and equation (10) is further simplified as:

$$\begin{cases} z - z_0 = OPL/n_c \cdot \cos(\theta_{in} - \theta_r) \\ x = x_0 - \dfrac{\partial z_{EPI}}{\partial x}(OPL/n_c^2 + z - z_0) \\ y = y_0 - \dfrac{\partial z_{EPI}}{\partial y}(OPL/n_c^2 + z - z_0) \end{cases} \quad (11)$$

Figure 3:
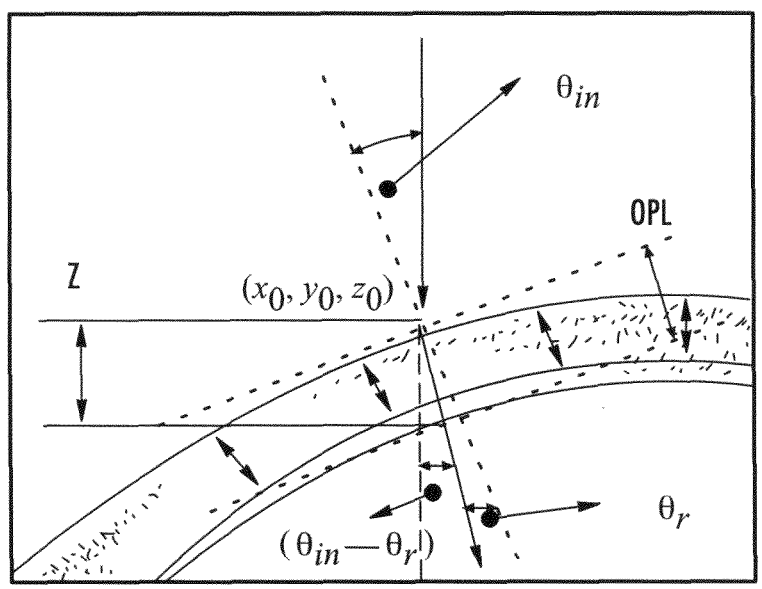
FIG. 3 illustrates three-dimensional refraction correction method parameters according to the present subject matter.

FIG. 3 provides illustrative definitions of the parameters in Equations (10-11). In particular, FIG. 3 illustrates the 3D refraction correction method parameters, which can be as follows:

$\theta_{in}$: Incidental angle;
$\theta_r$: Refraction angle;
OPL: Optical path length in OCT image; and
z: The projection of OPL on the z-axis.

The 3D refraction corrected volume can then be generated by applying Equations (10-11) to each desired voxel subsequent to the refracting surface in a 3D volumetric dataset. Equations (10-11) can enable practical 3D refraction and index of refraction variation correction of volumetric OCT datasets.

Many scanning patterns can be employed in ophthalmic imaging. One common scanning pattern can be raster scanning (a stack of sequential B-scans is used to form a box of images) and another common scanning pattern can be radial scanning (each B-scan is centered around a rotational axis). The advantage of the raster scanning is that it provides complete and evenly sampled x, y, and z data throughout the volume. For example, each B-scan exists in the x-axis, the stacking of B-scans creates the y-axis, and the individual points in an A-scan define the z axis. This is ideal for Cartesian implementation of the 3D refraction correction. While the radial scanning pattern has the advantage of high SNR for all B-scan frames, the data is generally asymmetrically sampled with denser sampling centrally and less peripherally. For a Cartesian implementation as in equation (10), this requires that the data first be interpolated and then resampled evenly. One such implementation is via Zernike fitting as described below. Alternatively, a polar implementation of equation (6) can be created.

Figure 4A:
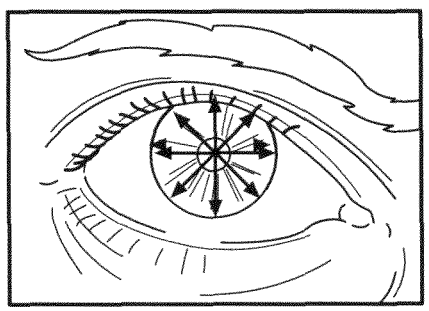
FIG. 4A illustrates an embodiment of a corneal scanning pattern in the form of a radial scanning pattern with each B-scan passing through the apex according to the present subject matter.
Figure 4B:
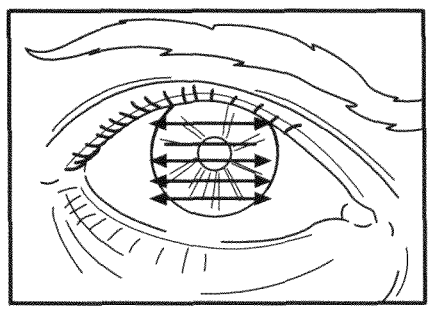
FIG. 4B illustrates an embodiment of a corneal scanning pattern in the form of a raster scanning pattern according to the present subject matter.

Examples of these two different scanning patterns are illustrated in FIGS. 4A and 4B. In particular, FIG. 4A illustrates a radial scanning pattern with each B-scan passing through the apex. FIG. 4B illustrates a raster scanning pattern.

Although these are two of the more common scanning patterns, it should be understood that scanning can comprise other patterns of B-scans designed for optimal coverage of the area of interest in the anterior segment. Alternatively, the dataset may comprise multiple individual A-scans distributed around the eye's surface in such a way as to maximize the concentration of image data in regions of particular clinical interest or in such a way as to minimize image artifacts such as caused by motion of the patient during data acquisition. Such patterns of individual A-scans can place them in radial, circular, raster, or random patterns, or patterns that contain repeated or nearly repeated sequences of sub-patterns designed to minimize the effects of patient motion.

2. Zernike 3D Interpolations
2.1. Zernike 3D Interpolations for Raster Scanning Pattern One issue with the newly generated, 3D refraction corrected volumetric data can be that the pixels are no longer evenly sampled. As such, a means to evenly resample such data for further analysis and visualization can be devised. For example, the complete endothelial surface can be reconstructed to obtain a corneal thickness map (each epithelial normal may no longer intersect a physical endothelial pixel) or to generate wavefront aberration analyses of the endothelium. To reconstruct even-sampled epithelium and the endothelium surfaces, a Zernike polynomial 3D interpolation can be employed to obtain the even-grid epithelial, uncorrected endothelial and refraction corrected endothelial surfaces. By using Zernike interpolation to reconstruct the surfaces, image re-segmentation from the newly generated refraction corrected volumetric dataset can be avoided.

Zernike polynomials are a set of complete orthogonal polynomials defined on a unit circle. These polynomials are represented in polar coordinates by:

$$Z_i(r, \theta) = R_n^{|m|}(r)\Theta^m(\theta) \quad (12)$$

$$R_n^{|m|}(r) = \sum_{s=0}^{(n-|m|)/2} \frac{(-1)^s \sqrt{n+1}\,(n-s)! r^{n-2s}}{s![(n+m)/2 - s]![(n-m)/2 - s]!} \quad (13)$$

$$\Theta^m(\theta) = \begin{cases} \sqrt{2}\cos|m|\theta & (m > 0) \\ 1 & (m = 0) \\ \sqrt{2}\sin|m|\theta & (m < 0) \end{cases} \quad (14)$$

$$A(Rr, \theta) = \sum_{i=0}^{\infty} c_i Z_i(r, \theta) \quad (15)$$

$$c_i = \frac{1}{\pi}\int_0^{2\pi}\int_0^1 A(Rr, \theta) Z_i(r, \theta) r\, dr\, d\theta \quad (16)$$

Where the indices n and m are the radial degree and the azimuthal frequency respectively; i is a mode-ordering number; R is used to normalize the measurement data to a unit circle and $c_i$ is Zernike elevation interpolation coefficients.

Figure 5A:
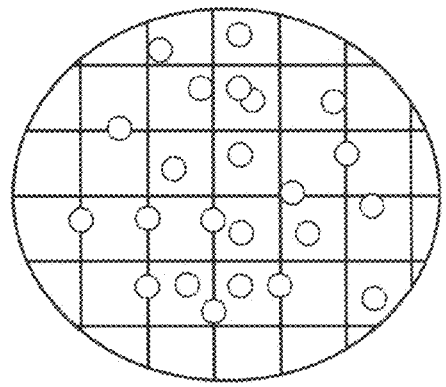
FIG. 5A illustrates an embodiment of refraction corrected voxels (e.g., voxels on the endothelial surface) no longer on an even sampling grid after a 3D Snell's law correction according to the present subject matter.
Figure 5B:
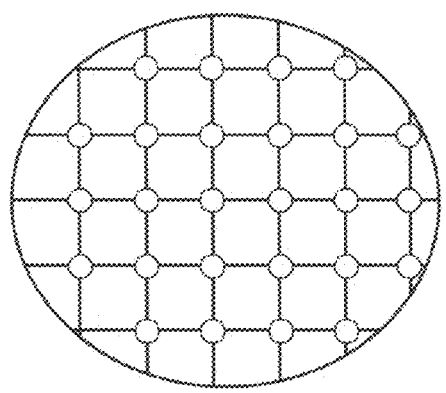
FIG. 5B illustrates an embodiment of a Zernike 3D interpolation with regenerated evenly sampled voxels according to the present subject matter.

FIGS. 5A and 5B show the procedure for Zernike 3D interpolation. In FIG. 5A, the volumetric pixels, or voxels, from the 3D refraction corrected volumetric data are not evenly sampled. In particular, the refraction corrected voxels (e.g., voxels on the endothelial surface) are no longer on an even sampling grid after 3D Snell's law correction. Through the use of the Zernike polynomial 3D interpolation, the voxels from the 3D refraction corrected volumetric data can be evenly sampled again as shown in FIG. 5B. Thus, any elevation value of arbitrary points can be obtained using Zernike interpolation coefficients.

Figure 6A:
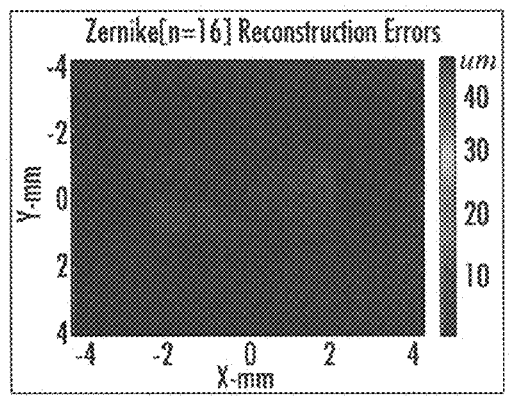
FIG. 6A illustrates the accuracy of an embodiment of a Zernike 3D interpolation in which the mean Zernike 3D interpolation errors are less than 0.9 micrometers within a diameter 4-millimeter according to the present subject matter.
Figure 6B:
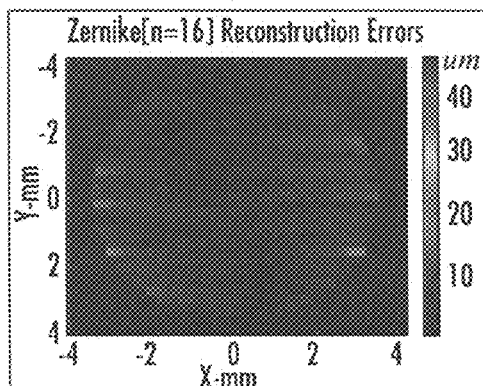
FIG. 6B illustrates the accuracy of an embodiment of a Zernike 3D interpolation in which the mean Zernike 3D interpolation errors are less than 2.8 micrometers for 7-millimeter diameter according to the present subject matter.

Since OCT can employ a very dense scanning pattern containing more than ten thousand points, the 3D Zernike interpolation can provide a good interpolation of the corneal surface without loss of accuracy. For instance, using a 16 order Zernike polynomial fit, the mean fitting (residual) error can be 0.9 micrometers within a 4-millimeter diameter and 2.8 micrometers for a 7-millimeter diameter. FIGS. 6A and 6B show the Zernike 3D interpolation errors. In FIG. 6a, the mean Zernike 3D interpolation errors are less than 0.9 micrometers within a diameter 4-millimeter. In FIG. 6B, the mean interpolation errors are less than 2.8 micrometers for 7-millimeter diameter. Both interpolation errors are within the range of the light source coherence length of 6.4 micrometers.

Since these errors are much less than the coherence length of 6.4 micrometer, the Zernike 3D interpolation is acceptable for clinical applications. By using Zernike coefficients in representing corneal surfaces also can provide the following advantages.

(1) For large data volumes, only Zernike coefficients (less than 200 float points) can be used to significantly compress the data scale.
(2) The coefficients only represent the particular surface but not the other layers. Hence, image re-segmentation is unnecessary.
(3) The coefficients provide the elevation of any arbitrary point, which intrinsically avoids the additional interpolation steps when trying to find the intersection points between anterior surface normals and the posterior surface.

It is not necessary to do the 3D interpolation for the epithelial surface in the raster scanning pattern as it is already evenly sampled.

2.2. Zernike 3D Interpolations for Radial Scan Patterns

Figure 7A:
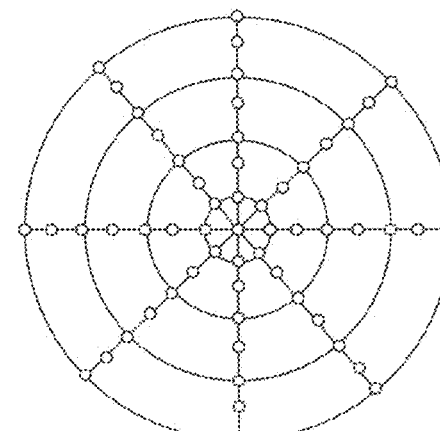
FIG. 7A illustrates an embodiment of the re-sampling issue in the radial scanning pattern according to the present subject matter.
Figure 7B:
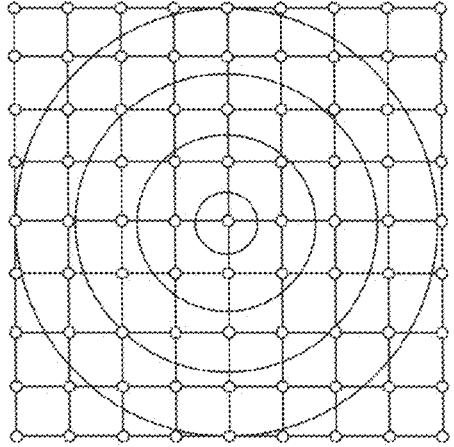
FIG. 7B illustrates an embodiment of a re-sampling of a radial scanning pattern with a Zernike polynomial even-grid interpolation based on the noneven-grid radial sampling points according to the present subject matter.

Similarly, Zernike 3D interpolation can be performed for all surfaces in non-raster scan patterns (such as radial scan patterns). In a radial scan pattern, the central area of the scan can be sampled more densely than that in the periphery. FIGS. 7A and 7B illustrate the sampling density in radial scanning cases. FIG. 7A shows a radial scanning pattern. As can be seen, the sampling density is different between central and peripheral points. Specifically, the sampling points are much sparser in the outer circles than in the inner circles.

FIG. 7B shows a Zernike polynomial even-grid interpolation performed for a surface that has been sampled radially for both the epithelium and endothelium surfaces based on the noneven-grid radial sampling points. This applies to all scan patterns which sample unevenly (with respect to x and y).

The interpolation procedure for this case is summarized as following:
(1) Segment both the epithelium and endothelium surface.
(2) Employ an 8th-order Zernike polynomial fitting to interpolate both surfaces into an even-grid sampling space.
(3) Calculate the surface partial differential equations of the epithelial surface.
(4) Use equation (10) to obtain the refraction corrected endothelium surface.
(5) Utilize the Zernike 3D interpolation again to reconstruct the refraction corrected endothelial surface.

Figure 8:
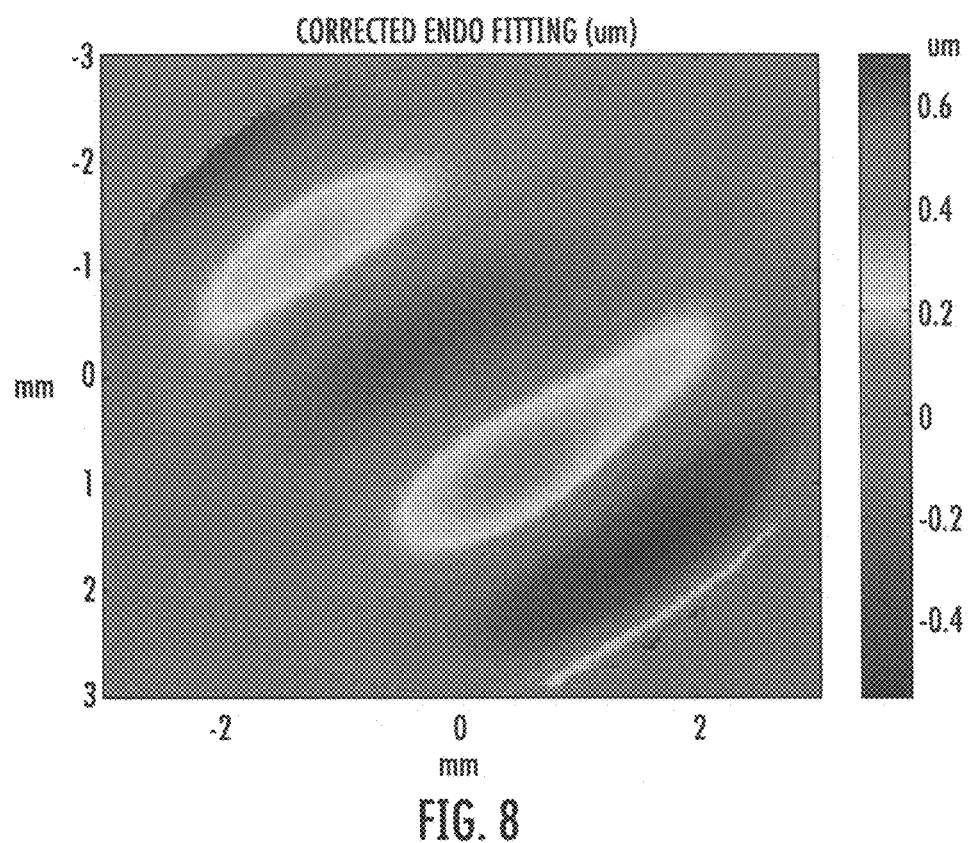
FIG. 8 illustrates an embodiment of residue errors from after $8^{th}$ order Zernike fitting of the refraction corrected inner surface of a rigid contact lens according to the present subject matter.

FIG. 8 shows an example of 8th-order Zernike fitting residue errors of refraction corrected endothelium surface of a rigid contact lens. The maximum fitting errors can be less than 0.7 micrometers. While the use of Zernike functions represents a particularly attractive solution to re-sampling the optically refracted data points to an evenly sampled grid, it should be understood that any number of other re-sampling techniques which are well known in the art may also be used for this purpose.

3. Other Data Correction

Instrument mis-calibrations and non-linearities can be rectified by careful calibration of the instrument on a calibration target of known dimensions prior to patient imaging, including calculation of correction factors to be applied to the resulting image data. Correction for patient motion or loss of fixation can be rectified by employing methods to estimate the actual patient head or eye motion which occurred during image acquisition, and then using this information to correct the resulting image data. Methods to estimate the actual patient motion can comprise external instrumentation such as an iris camera or eye tracker (both used to estimate lateral or rotational eye motion), or can comprise image processing methods such as image registration to estimate axial or lateral motion in OCT A-scans, B-scans, or volume scans.

For example, patient axial or lateral motion between B-scans can be estimated from the peak of the normalized cross-correlation between sequential A-scans (for axial motion), B-scans (for axial and lateral motion in the direction of the B-scan), or volume scans (for axial and lateral motion, assuming the volume scans are acquired quickly compared to the patient motion). Many other image registration and motion estimation algorithms are well known in the art of image processing and can be used for this purpose. Once estimates of axial or lateral motion are obtained, they can be used to correct the volumetric image dataset by re-positioning image data within the dataset to its true position. Also, if the image dataset contains missing image data (e.g., because the patient blinked or because lateral motion resulted in some areas of the sample not being undersampled), such data can be filled in by image interpolation algorithms. Other bulk motion methods can include analyzing the natural motion frequency of the patient. Then the sampling frequency can be adjusted to any high order harmonic frequency of the patient motion. In this way, it is possible to statistically reduce the patient motion.

Correction of image artifacts can be done as just described upon the raw A-scan, B-scan, or volumetric image datasets, creating corrected image datasets before further segmentation and image processing. Alternatively, rather than creating entirely new corrected image datasets, it can be possible and computationally simpler to perform some artifact correction operations upon partially processed data, such as segmented data.

Correction of some image artifacts, such as those resulting from axial or lateral patient motion or missing data, can be accomplished at this point when the entire image dataset has been reduced to a mathematical surfaces model. For example, a simple but effective method for correction of axial patient motion during sequential radial B-scan acquisition comprises registering the segmented corneal anterior surface of each radial B-scan to that of a selected reference B-scan (e.g., the first one in the set) at a selected lateral location within each B-scan (e.g., its center pixel). This axial motion estimate can then be applied to correct the entire mathematical surface model such that the center of each radial B-scan is at the same axial location. This method is expected to work well when the axial component dominates patient motion during data acquisition.

4. Clinical Parameter Computation: Corneal Thickness Mapping, Wave Aberration Analysis, Asphericity Analysis, Refractive Curvature Maps, Float Maps, and Others 4.1 Corneal Thickness Mapping A corneal thickness map can be created by determining the normal distance between the epithelial and endothelial corneal surfaces in the volumetric surface model via an analytical or numerical approach. As used herein, the term normal can be defined as normal to the epithelial surface. There can be a thickness value for each pixel representing the epithelial surface. The thickness value for each pixel can be mapped to a color scale to produce a two-dimensional pachymetry (thickness) map.

The corneal thickness is measured along the epithelial surface normal vector. The surface normal equation of the epithelium is obtained by:

$$\frac{(x - x_0)}{\partial F(x, y, z)/\partial x} = \frac{(y - z_0)}{\partial F(x, y, z)/\partial y} = \frac{(z - z_0)}{-1} \quad (17)$$

Where $(x_0, y_0, z_0)$ stands for the coordinate of point C; and $(x, y, z)$ stands for the coordinate of an arbitrary point on the normal equation (line).

It can be difficult to derive an analytical solution between equation (17) provided above and equation (18) provided below. A numerical solution called the recursive half searching algorithm ("RHSA") and method can be used here to solve for $(x, y, z)$ that exists within a defined distance (e.g., an error tolerance) to the endothelial surface. RHSA starts with an estimate of where the endothelial pixel should be along the normal line that was calculated as part of the 3D refraction correction. If that estimate does not exist on the prior Zernike interpolation of the endothelial surface, it will be off by some amount in the z direction. That amount is halved and used as the next estimate of the endothelial pixel. The process is repeated until the difference between the estimate and the surface is less than the desired error.

Figure 9:
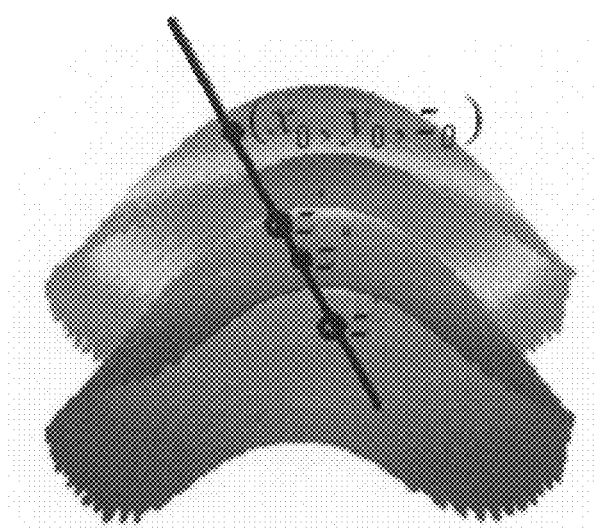
FIG. 9 illustrates a top surface of an epithelium and a second surface of an endothelium according to the present subject matter.

For instance, if the error tolerance is 0, then $(x, y, z)$ will be coincident with the endothelial surface. An appropriate error tolerance is chosen to balance clinical needs and computation time. The principle is illustrated in FIG. 9 of searching intersection points between the surface normal equation of epithelial and refraction-corrected endothelial surface. In FIG. 9, the top surface is epithelium and the second is endothelium. The syllables illustrated in FIG. 9 are as follows:

z': Obtained using equation (16) after half distance recursion; and z": retrieved using Zernike coefficients in equation (15).

Thus, RHSA permits searching for the normal (perpendicular) distance between two surfaces given known spatial coordinates of the first surface and given a representation of the second surface in a basis space. In this particular implementation, the basis functions are Zernike polynomials, and the RHSA permits searching for the intersection between the epithelial surface on the normal equation and the endothelium.

The starting guess point can be the refraction uncorrected endothelium (x,y,z). The new coordinates of (x,y,z) of the first step can be estimated by manipulating equation (17):

$$\text{Step 1:} \begin{cases} z' = z(\text{uncorrected endothelium position}) \\ x' = x_0 - \partial F(x, y, z)/\partial x_{(x0,y0,z0)}(z' - z_0) \\ y' = y_0 - \partial F(x, y, z)/\partial y_{(x0,y0,z0)}(z' - z_0) \end{cases} \quad (18)$$

$\partial F(x,y,z)/\partial x_{(x0,y0,z0)}$ and $\partial F(x,y,z)/\partial y_{(x0,y0,z0)}$ can be the constant partial derivatives of the epithelial surface at point C, and they do not need to be calculate again. In step 2, it can be determined if the new point (x', y', z') is located at the Zernike interpolated endothelial surface.

Step 2: (19)

$$\begin{cases} z'' = \sum_{i=0}^{\infty} c_i Z_i(r(x', y', z'), \theta(x', y', z')) \\ \text{if } |z' - z''| \leq \varepsilon, \text{ then stop and } (x', y', z') \text{ will be the target point} \end{cases}$$

$\epsilon$ is the stop condition (i.e., the error tolerance), which can be defined as 1 micrometer in some examples. Step 3 will be followed if it does not reach the convergent accuracy.

Step 3: (20)

$$\begin{cases} \text{if } |z' - z''| > \varepsilon \text{ then} \\ z' = z' + |z' - z''|/2 \text{ if } z' < z'' \quad search point is below endothelium \\ z' = z' - |z' - z''|/2 \text{ if } z' > z'' \quad search point is above endothelium \\ Repeat Step 1 \text{ and } Step 2 \end{cases}$$

The above search method can be used to recursively halve the difference of the search distance. Hence, it can converge very fast and only needs 6 steps to define the intersection point.

Once each epithelial point in the modeled surface has a thickness value calculated for it, the values can be fit to a color scale. A typical color scale can represent average corneal values (around 500-600 μm) as green with thinner values trending warmer (red) and thicker values trending cooler (blue).

The data can then be plotted as a two-dimensional map providing an en face (looking coincident with the direction of the visual axis) view corneal map. This concept of thickness mapping can be applied to any two desired surfaces, for instance the thickness of the human lens can be measured between the front and posterior lens surfaces as imaged by SDOCT. This could also be applied to the magnitude of spaces between two surfaces. For instance, the anterior chamber depth can be defined as the distance between the corneal endothelial surface and the anterior lens surface (or iris in the periphery or an anterior chamber lens if present).

Figure 10A:
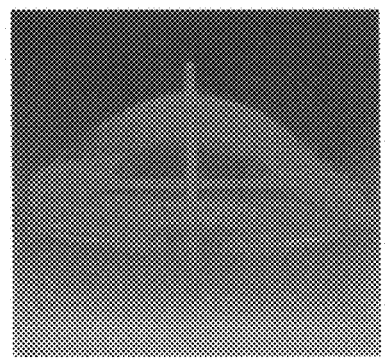
FIG. 10A illustrates a 3D volume of raw corneal data where the DC lines form a horizontal plane according to the present subject matter.
Figure 10B:
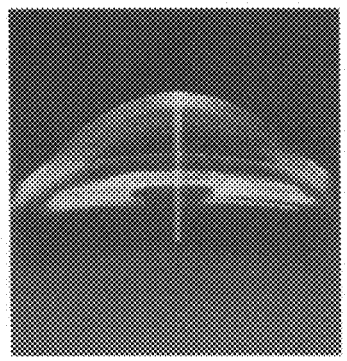
FIG. 10B illustrates a 3D refraction corrected volumetric dataset where the corrected DC lines form a curved plane according to the present subject matter.
Figure 10C:
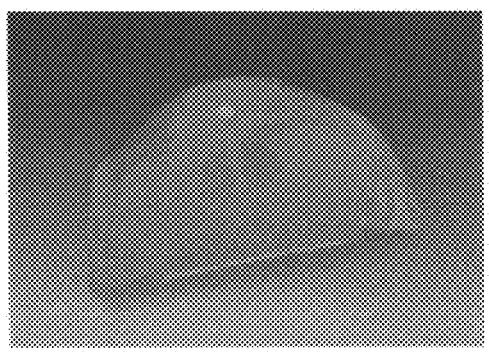
FIG. 10C illustrates a 3D corrected volume in another view angle according to the present subject matter.
Figure 10D:
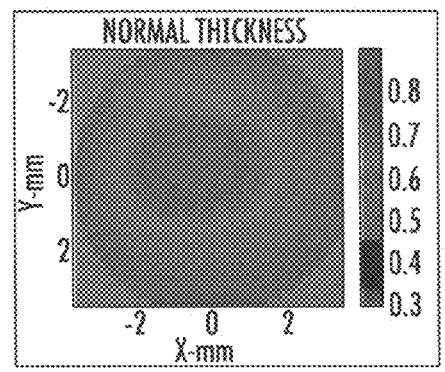
FIG. 10D illustrates a normal thickness map of a subject's cornea generated via the RHSA method according to the present subject matter.
Figure 10E:
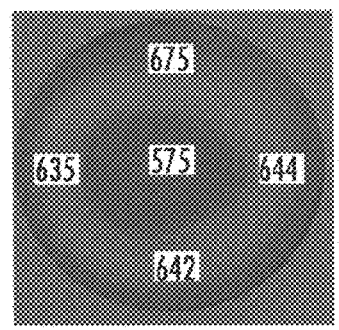
FIG. 10E illustrates a thickness mapping of the cornea shown in FIGS. 10A-10C obtained by a reference instrument (Oculus Pentacam)
Figure 10F:
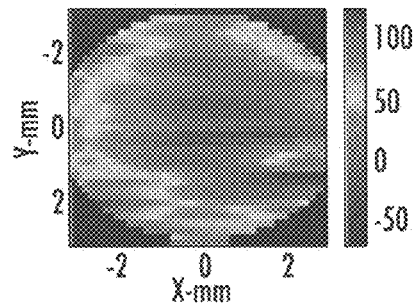
FIG. 10F illustrates thickness mapping differences between 2D and 3D Snell's law according to the present subject matter.
Figure 11:
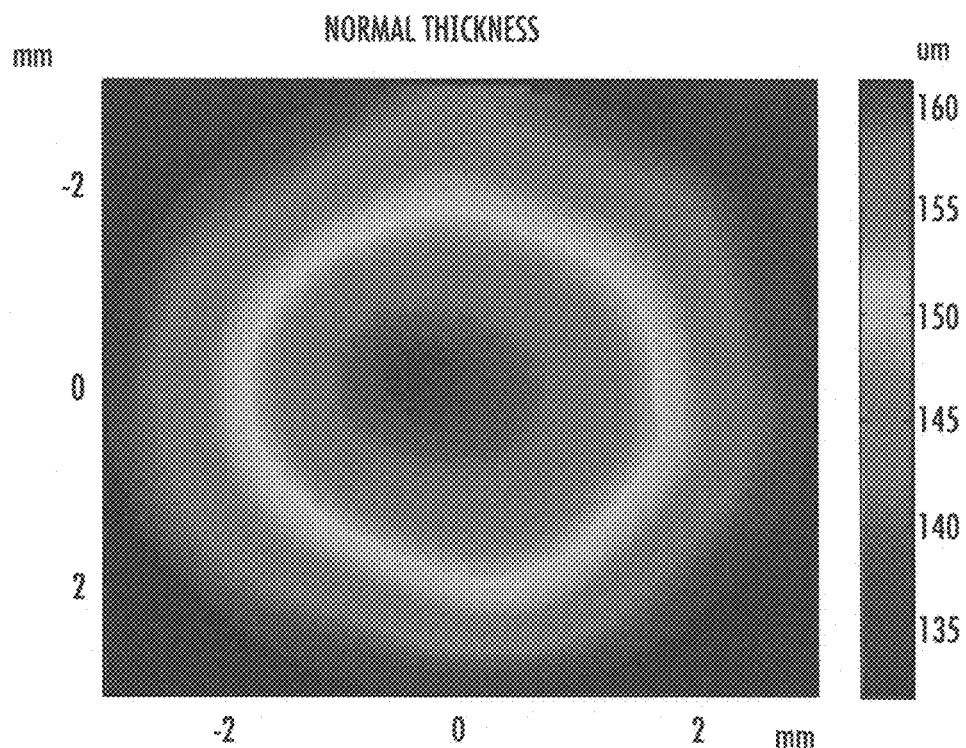
FIG. 11 illustrates a computed thickness of a phantom rigid contact lens with radial scanning pattern according to the present subject matter.
Figure 12:
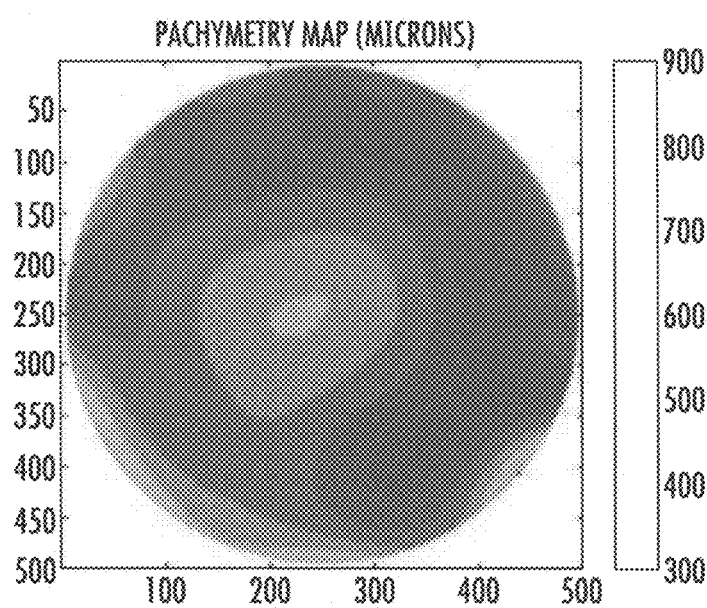
FIG. 12 illustrates a computed normal thickness map from spectral domain optical coherence tomography data of an in vivo subject with the RHSA method according to the present subject manner.

FIGS. 10A-10F illustrate example 3D refraction correction results. FIG. 10A illustrates a raster scanned 3D raw corneal volumetric dataset without refraction correction. As illustrated, all DC lines (i.e., artifacts in SDOCT images which are perpendicular to the axis of illumination of the sample) form a horizontal plane. After 3D refraction dewarping, the corneal volume can be shrunken in the x, y and z dimensions simultaneously as shown in FIG. 10B. As shown in FIG. 10B, the horizontal plane formed by DC becomes curved after the refraction correction. FIG. 10C shows a 3D visualization from a different viewing angle. FIG. 10D shows the thickness mapping via RHSA method. The Oculus Pentacam measurement result of the same cornea is displayed in FIG. 10E (Pentacam is an accepted commercial instrument which measures corneal thickness using a different method than OCT). In this illustration, the difference between the OCT and Pentacam measurement at the apex is 8 micrometers which is within the measurement accuracy (50 micrometers) of Pentacam. FIG. 10F indicates the difference in thickness mapping between 2D and 3D refraction correction. The mean difference between 2D and 3D Snell's law correction is 34 micrometers with a standard deviation of 30 micrometers. The mean difference is large enough to be of clinical significance. For example, the corneal thickness map was smoothed by a 2-dimensional low-pass image filter. FIG. 11 shows the thickness map of a phantom rigid gas permeable contact lens using a radial scanning pattern. FIG. 12 shows a thickness (pachymetry) map of an in vivo human cornea derived from spectral domain optical coherence tomography acquired volumetric dataset of a subject.

Another method for determining the normal distance between the epithelial and endothelial corneal surfaces can be to use ray tracing and Newton's algorithm to find the intersection point along the Newton search direction.

$$\text{Newton Search Direction} = \left[\frac{\partial G(x, y, z)}{\partial x}l, \frac{\partial G(x, y, z)}{\partial y}m, \frac{\partial G(x, y, z)}{\partial z}n\right] \quad (21)$$

G(x,y,z)=0 is the implicit form of the endothelium and the direction cosines of the epithelial surface normal equation is represented in (l.m.n) which is related to the epithelial surface derivatives. This method requires iterative calculation of all the partial derivatives, $$\left[\frac{\partial G(x, y, z)}{\partial x}, \frac{\partial G(x, y, z)}{\partial y}, \frac{\partial G(x, y, z)}{\partial z}\right]$$

of the intermediate approximation points on the endothelium. Thus, this method can be considered computationally more intensive. In addition, the intermediate partial derivatives of the endothelial surface are much more sensitive to the noise which influences the convergence.

Still other methods which are well known in the art may be applied for determining the normal distance between the epithelial and endothelial corneal surfaces following 3D refraction correction.

4.2 Corneal Wavefront Aberration Analysis

After 3D refraction correction, the individual wavefront aberration of the epithelium and endothelium layers can be estimated. Similar to the method employed in professional optical design software Zemax™, the optical path differences, also called wavefront aberrations $W_a$, between the off-axis and on-axis for the all meridians are calculated within 7-millimeters. Equation (22) gives the computing method.

$$W_a = n_{Cornea} \cdot f - n_{Air} \cdot Z_a - n_{Cornea} \cdot d \quad (22)$$

$$C_i = \frac{1}{\pi}\int_0^{2\pi}\int_0^1 W_a(Rr, \theta)Z_i(r, \theta)r\,dr\,d\theta \quad (23)$$

$C_i$ describes the wavefront aberration coefficients. For example, $C_{13}$ (with mode index=1) is called spherical aberration error. The wavefront aberration analysis using Zernike spectrum analysis and ray tracing is illustrated in FIGS. 13A and 13B. In FIG. 13A, the anterior surface corneal height is labeled $Z_a$; f is the distance of the focus point (F) to the apex of the surface VA; and d is the distance of this focus point to an arbitrary point on the surface. FIG. 13B shows the Zernike aberration analysis of the cornea. Red is for anterior surface and green is for posterior surface. Overall the anterior surface contributes much more aberration errors than that of posterior surface. The spherical aberration error of the epithelium is around 1.1 micrometers and −0.6 micromeres for the endothelium.

4.3 Asphericity, Refractive Curvature, and Best Fit Sphere Analysis

Asphericity and best sphere fitting can be used to estimate the asphericity, surface curvature, and to create float maps.

Asphericity (K) and the radius of curvature for a surface (R) can be obtained using 3D fitting with Equation (1). Using a phantom contact lens, the measurement error of the base curvature from that reported for the phantom was less than 2.9%. The radius of curvature can be used to describe the refractive power of the cornea either over an optical region (for instance, refractive power within the central 3 mm optical zone) or locally over the entire cornea to produce a local refractive curvature map.

Best sphere fitting can be retrieved using 3D fitting by simply letting K=1 in equation (1). Examples of the results are demonstrated in FIGS. 14A-14D. Float images of different 3D fitting of a phantom contact lens are shown therein. FIG. 14A shows a float image of the anterior surface of a contact lens with asphericity fitting. In FIG. 14A, the asphericity is 0.8 and radius is 10.03 mm. FIG. 14B shows a float image of the posterior surface of a contact lens with best sphere fitting. FIG. 14C shows a float image of the posterior surface of a contact lens with asphericity fitting. In FIG. 14C, the asphericity is 0.59 and radius is 9.32 mm. FIG. 14D shows a float image of the posterior surface of a contact lens with best sphere fitting. The residuals demonstrate the amount of deviation of the corneal surface from that of the best fit sphere. This can be a clinically important indicator of ecstatic corneal conditions.

Elevation (float) maps can represent the distance between the modeled surface and a reference surface. For example, a sphere can serve as the reference surface, although any surface could be used (e.g., ellipsoids, other toric surfaces, defined planes). In the case of a reference sphere, the sphere can be chosen to best fit the modeled surface within a defined area of that surface. Corneal elevation maps can be created by first designating a reference surface. The reference shape can be chosen as a standard shape (e.g., a planar or spherical surface) or other surface shape chosen to fit the modeled corneal surface. The deviation in the z-axis (nominally the same direction as the visual axis) of each pixel in the modeled corneal surface from the reference surface can be designated as the elevation value. The pixel elevation values can again be mapped to a color scale to produce this two-dimensional map.

Returning again to Equation (1), by setting K to 1, the surface is modeled as spherical. Other values deform this surface into various ellipsoids. For this particular implementation, $(x_0, y_0)$ can be assigned to either the center of the dataset or allowed to "float" such that there are no constraints on the location of this apex. The (x, y, z) values of the modeled surface within the area of desired fitting can then be used to solve for R (and $x_0$, $y_0$, $z_0$ if unconstrained) using a curve fitting algorithm (e.g., least squares).

Figure 16:
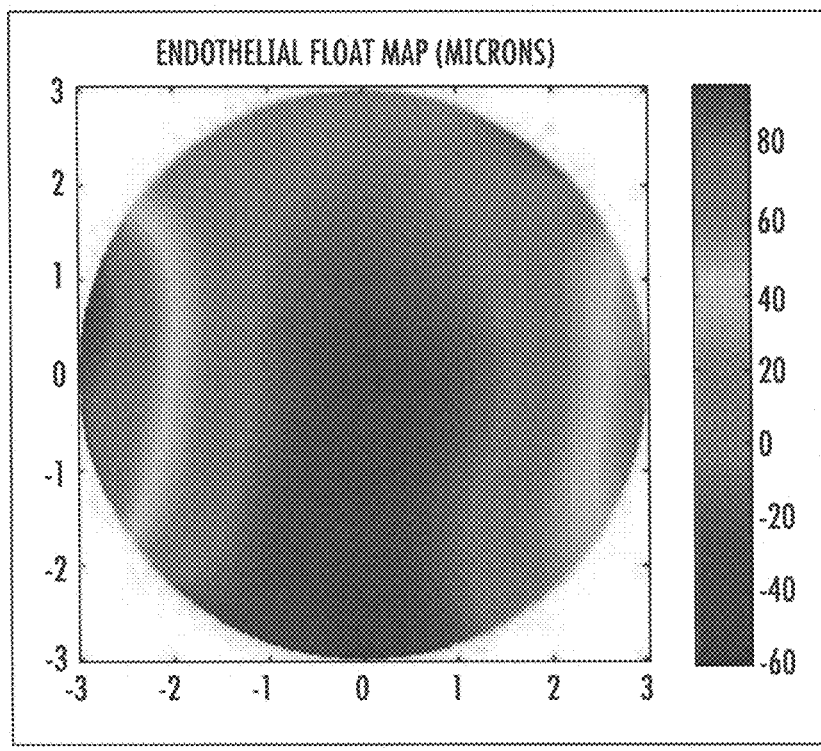
FIG. 16 illustrates an float map (difference map of imaged surface against a reference surface—here a best fitting sphere) of the posterior endothelial surface of an in vivo human cornea as derived from a SD-OCT-acquired volumetric dataset of a subject.

With K set to 1, this solution represents the best fitting sphere for the modeled surface within the desired area and the residuals from the fitting represent the deviation in the z-axis of the modeled surface at each (x, y, z) from the best fitting sphere. These residuals can be fit to a color scale and plotted to provide a two-dimensional en face view of the elevation data, such as is shown in FIG. 16. This type of referenced elevation map can be created for any desired surface derived from OCT images (corneal epithelial surface, endothelial surface, lenticular surfaces, etc.).

Regarding curvature and power maps, previous methods for calculating curvature values were based on estimates of radii of curvature of the corneal epithelial surface using reflection based imaging technologies. With OCT, however, curvature values of any surface or combination of surfaces can be produced. For instance, a corneal curvature map can be created by determining the radii of curvature at each local point (defined by some local radius, typically 0.1-1 mm) on the modeled surfaces. Radii of curvature of the modeled corneal epithelial surface can be determined from the best fitting sphere as in elevation mapping for small discrete, defined regions on the surface (e.g., regions that are 1 mm in diameter). The radii of curvature can then be converted into dioptric power by convention using the following equation:

$$Power = \frac{n_{keratomtric} - 1}{r_c} \quad (24)$$

Here, $r_c$ is the radius of curvature in mm within the discrete area and $n_{keratometric}$ can either be an accepted value (such as one to equate a $r_c$ of 7.5 mm with 45 D) or empirically derived to yield other dioptric power to $r_c$ associations.

There are multiple alternative ways to constrain the local surface fitting. The tangential curvature method can allow for the best fitting sphere/curve for the sampled surface area. The axial curvature method can constrain the origin of the radius of curvature of the best fitting sphere/curve to the visual axis. In this case, for equation (1), the radius of curvature would be explicitly stated to always originate at $(x_0, y_0)$.

With an evenly spaced sampling of the radii of curvature across the epithelial surface, the values can be fit to a color scale and plotted to provide a two-dimensional en face representation of curvature with interpolation as required if the sampling is insufficiently dense. Multiple color scales are available in the literature including those created by standards bodies.

Figure 15:
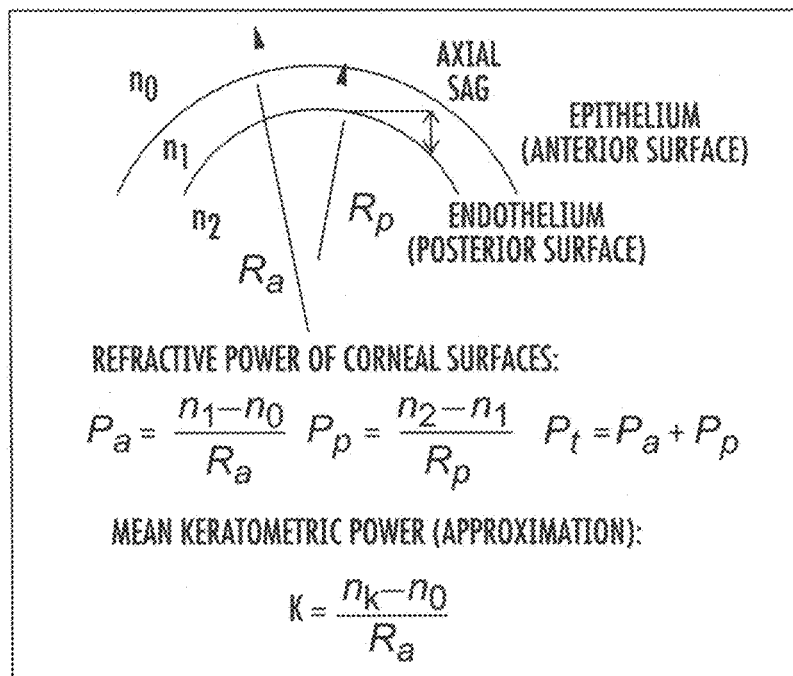
FIG. 15 illustrates the cornea modeled as a thin lens and the relationship between the radii of curvature and the calculation of refractive power.

The radii of curvature may then be converted to ophthalmic diopter powers, which can be inversely related to the radii according to the formulas in FIG. 15. This can be done using curvature data from each of the two corneal surfaces. Alternatively, the so-called "keratometric" dioptric power of the cornea can be estimated from the radius of curvature of the epithelial surface only by assumption of a so-called keratometric index of refraction $n_k$. As shown in FIG. 15, $R_a$ and $R_p$ are the radii of the corneal anterior and posterior surfaces, which are often assumed to be spherical. The relevant refractive indices are $n_0$=1.0 (air), $n_1$=1.376 (corneal stroma), $n_2$=1.336 (aqueous humor), and $n_k$=1.3375 (keratometric index). The curvatures and ophthalmic (refractive) powers thus calculated for each pixel or local region on the cornea can then be mapped to a color scale to produce two-dimensional representations of curvature and power, respectively.

For the specific case in which the surface area of the cornea to be fitted is centered on the visual axis, this power can provide a summary estimate of corneal optical power through the thin lens equation. This area can typically be around 3-4 mm in diameter, as this is the region of the cornea which is most spherical and thus most amenable to the spherical model described by radii of curvature. This calculation requires derivation of the radius of curvature of both the anterior and posterior surfaces.

The above analyses (thickness, elevations and curvatures, estimated optical power) can also be performed for OCT images of the human lens. Because OCT provides a full volumetric rendering of both surfaces of the cornea, independent radii of curvature of both the anterior and posterior surfaces centered on any arbitrary axis can be calculated. If these axes are sampled evenly across the cornea, a full map of physical (in contrast to keratometric) power of defined sampled areas could be created similar to the maps described above (fit to color scale and display en face).

Further, OCT images that contain both the cornea and lens (either registered or in whole) can be used to create power maps describing the two refractive components of the human eye. These can be summed with appropriate optical treatment via ray tracing to determine the power contributions of the cornea and lens in the visual axis or any arbitrary desired axis. Unique, novel parameters such as percentage contribution of the corneal power (i.e., lenticular power) to the total power (i.e., cornea power plus lens power) can be calculated and fit to a color scale such that 50% is centered on green with warmer colors representing greater contribution of that component versus cooler colors representing lesser contribution of that component. This analysis can provide information for surgeons planning selective refractive procedures (e.g., cornea or lens based).

As the cornea and lens comprise the main refractive components of the eye, analysis of both components from OCT images (singly and in combination as in power maps centered on designated axes as in the visual axis) can provide valuable information regarding the refractive status of the eye. For volumetric OCT images of the anterior segment that comprise the irido-corneal angle, a similar map can be created of the magnitude of the angle or any numerical parameter derived from images of the irido-corneal angle (such as a specific defined 2-D area of the angle within the image, distance of the iris to the cornea at a specified distance from the apex of the angle).

4.4 Other Clinical Analyses

Given an anatomically accurate, 3D refraction corrected representation of the eye, other analyses can be carried out.

For instance, the angle between the iris and the adjacent corneal endothelial surface can be an important parameter in glaucoma care. An accurate volumetric dataset can be used to create an en-face map of the magnitude of these angles. Multiple radial samplings of the intersection of the iris and adjacent corneal endothelial surfaces can be used to derive vectors from which the angle between them can be calculated. Similarly, the angle could also be described as any numerical quantity which describes the relevant clinical concept, such as the distance between the iris and cornea in this region and thus the gross physical availability of the trabecular meshwork. For instance, the triangular area with its apex at the apex of the angle and its base defined as the line normal to a fixed reference such as Schwalbe's line or simply the length of the base of this triangle. These samplings can then be mapped to their enface position. In contrast to current isolated local angle measurements, such an "angle map" can show regions of narrow angles or angle closure, which could be important to glaucoma management. The only current comparable clinical view would be direct manual visualization of the angle structures using a mirror and mentally (via drawing) recreating the observed degree of regional angle magnitudes. This type of en-face angle magnitude map display from tomographic image data has not been previously described.

3D displays of the anterior chamber space can also be created. These dimensions can be useful in planning for artificial lens placements both in the anterior chamber and posterior chamber.

If the OCT dataset includes data from the lens, the lenticular surfaces can also be serially refraction corrected using equation (9) at different locations. For example, the lenticular surfaces can be serially refraction corrected first at the corneal epithelium, then at the corneal endothelium, and then at the anterior lenticular surface. From the corrected data, wavefront aberration analyses of the lenticular surfaces as described above can be undertaken.

As provided above, methods and algorithms are provided for quantitative image correction and clinical parameter computation which is generally applicable for any OCT sample containing refracting interfaces and regions of different refractive indices. The methods and algorithms are particularly suitable for quantitative correction of 3D OCT images of the cornea and anterior segment of the eye. Two specific implementations for two different scanning patterns can be introduced for corneal imaging. Zernike 3D interpolation can be used to represent the corneal surfaces (epithelium, uncorrected endothelium, and refraction corrected surfaces). This interpolation method can make it possible for the implementation of a recursive half searching algorithm (RHSA) and method to measure the corneal thicknesses and map them in an en-face clinical view. 3D corneal volumetric refraction correction can provide the foundation for generating further clinical parameters. These comprise known clinical ones such as wavefront analysis, asphericity, refractive curvature maps, and best fit sphere float maps as well as novel ones such as angle magnitude maps. 3D refraction correction and the accurate representation of ocular structures it creates provide an important tool in the visualization and management of ocular disease.

Embodiments of the present disclosure shown in the drawings and described above are exemplary of numerous embodiments that can be made within the scope of the appended claims. It is contemplated that the configurations of methods for quantitative three-dimensional image correction and clinical parameter computation in optical coherence tomography can comprise numerous configurations other than those specifically disclosed.

What is claimed is:

1. A method for quantitative three-dimensional ("3D") image correction of optical coherence tomography (OCT) using a computer readable medium having stored thereon executable instructions, that when executed by a processor of a computer control the computer to perform the method comprising:
    calibrating a scanning system of an OCT imaging system by imaging a calibration target with known physical dimensions including deriving numerical correction factors that describe nonlinearities of the scanning system;
    obtaining a three-dimensional OCT image of a subject with the OCT imaging system;
    segmenting at least a first refracting surface interface from an OCT image dataset for the OCT image;
    correcting voxel positions for at least the segmented first refracting surface interface using the numerical correction factors derived during calibration; and
    calculating a refracted image voxel position for at least a portion of voxels in the OCT image dataset.

2. The method according to claim 1, further comprising repeating the steps of segmenting a refracting surface interface and calculating a refracted image voxel position until all desired refracting surfaces have been evaluated.

3. The method according to claim 1, wherein segmenting comprises identifying external and internal sample surfaces at which refraction occurs.

4. The method according to claim 3, wherein the sample surfaces comprise anterior and posterior surfaces of a cornea or a lens.

5. The method according to claim 3, wherein the step of segmenting comprises identifying locations within the sample at which to correct the OCT image dataset for refraction and index variations.

6. The method according to claim 5, wherein the identified locations comprise positions being at least one of below the first refracting surface or between all segmented refracting surfaces.

7. The method according to claim 5, wherein the identified locations comprise selected sample positions at which it is known that corrected data is to be obtained in order to calculate clinical parameters.

8. The method according to claim 1, wherein calculating refracted image voxel positions comprises calculating a normal vector or partial derivatives of curvature at each point on the segmented refracting surface where an OCT sample arm light strikes the sample.

9. The method according to claim 8, wherein calculating normal vectors or partial derivatives of the curvature at the refracting surface is dependent upon a scan pattern utilized to obtain the OCT image dataset and upon a coordinate system desired for conducting further computations.

10. The method according to claim 9, wherein the coordinate system is at least one of a Cartesian coordinate system or a polar coordinate system.

11. The method according to claim 10, wherein the coordinate system is a Cartesian coordinate system, and calculating normal vectors or partial derivatives of the curvature at the refracting surface comprises calculating the partial derivatives of the surface curvature in the x and y directions from surface normals.

12. The method according to claim 11, further comprising using a raster scan pattern oriented in the x or y direction to acquire data and calculating derivatives from one-dimensional polynomial functions fit using a least-squares fitting algorithm to each raster line in both orthogonal directions.

13. The method according to claim 11, further comprising using a radial scan pattern to acquire data and fitting surface points to a 3D Zernike polynomial model and subsequently calculating the surface derivatives at every point by at least one of analytically or computationally methods.

14. The method according to claim 11, wherein calculating normal vectors or partial derivatives of the curvature at the refracting surface comprises using an equation of:

$$\vec{MC} \times (-\vec{n}) \cdot n_{air} = \vec{CC'} \times (-\vec{n}) \cdot n_c$$

where $\vec{MC}$ comprises a direction vector (a,b,c) of incident light; × represents a vector cross product; $\vec{n}$ is a unit surface normal vector of an arbitrary incident point C; $n_{air}$ is refractive index of air; $\vec{CC'}$ is unit vector of a refracted ray; and $n_c$ is refractive index of subject and where calculations are applied after correcting the OCT image dataset for scanning non-linearities using the correction factors derived during calibration.

15. The method according to claim 14, wherein calculating normal vectors or partial derivatives of the curvature at the refracting surface comprises using equations of:

$$\begin{cases} z - z_0 = OPL/n_c \cdot \cos(\theta_{in} - \theta_r) \\ x = \dfrac{a * OPL}{n_c^2} + x_0 + \dfrac{\partial z_{EPI}}{\partial x}(c * OPL/n_c^2 - z + z_0) \\ y = \dfrac{b * OPL}{n_c^2} + y_0 + \dfrac{\partial z_{EPI}}{\partial y}(c * OPL/n_c^2 - z + z_0) \end{cases}$$

to calculate refraction corrected positions in x-, y-, and z-axes, where $C(x_0, y_0, z_0)$ is an incident point on an epithelium; $\theta_{in}$ is an incidental angle; $\theta_r$ is a refraction angle; OPL is an optical path length in an OCT image; and z is a projection of OPL on the z-axis and where calculations are applied after correcting the OCT image dataset for scanning non-linearities using the correction factors derived during calibration.

16. The method according to claim 1, wherein calculating the position of each desired refracted image voxel comprises generating a raw OCT image dataset comprising image brightness as a function of x, y, and z coordinates, a segmented image dataset of the index interface refracting surfaces comprising sets of the x, y, and z coordinates of the refracting surface, a set of surface normal vectors or partial derivatives of curvature of the refractive surfaces, and a set of incident light direction vectors and where calculations are applied after correcting the OCT image dataset for scanning non-linearities using the correction factors derived during calibration.

17. The method according to claim 16, wherein calculating the position of each desired refracted image voxel comprises producing a set of corrected x, y, and z coordinates of the corrected position of each desired image voxel beneath the refracting surface and where calculations are applied after correcting the OCT image dataset for scanning non-linearities using the correction factors derived during calibration.

18. The method according to claim 1, further comprising interpolating of new refracted corrected voxel positions to an even sampling grid comprising re-sampling refracted corrected voxel reflectivity data back to an original Cartesian sampling grid.

19. The method according to claim 18, wherein interpolating of new refracted corrected voxel positions to an even sampling grid comprises fitting corrected voxel data to a 3D Zernike polynomial model for re-sampling to a desired grid location.

20. The method according to claim 18, wherein interpolating of new refracted corrected voxel positions to an even sampling grid comprises generating a set of corrected x, y, and z coordinates of the new corrected position of each desired image voxel beneath the refracting surface and where calculations are applied after correcting the OCT image dataset for scanning non-linearities using the correction factors derived during calibraton.

21. The method according to claim 20, wherein interpolating of new refracted corrected voxel positions to an even sampling grid further comprises producing a set of interpolated corrected image brightness values as a function of x, y, and z coordinates of the even sampling grid.

22. The method according to claim 1, further comprising computing clinical outputs from corrected image data.

23. The method according to claim 22, wherein computing clinical outputs from corrected image data comprises producing a set of clinical output measures comprising numerical values, tables, graphs, images, and maps.

24. The method according to claim 22, wherein the OCT image dataset is of a cornea or a lens, and wherein computing clinical outputs comprises one or more of generating thickness maps, generating elevation maps, generating curvature maps, computing wavefront aberrations, or computing an angle between an iris and an endothelial surface.

25. The method according to claim 22, wherein the OCT image dataset is of a cornea and wherein computing clinical outputs from corrected image data comprises creating a corneal or lens thickness map by determining normal distance between the two surfaces in the volumetric surface model via an analytical or numerical approach.

26. The method according to claim 25, wherein a Cartesian coordinate system is used to conduct further computations and a recursive half searching algorithm ("RHSA") numerical solution is employed to solve within a predefined tolerance for perpendicular distances between discrete points of the epithelial surface and an interpolated second surface.

27. A method for quantitative three-dimensional ("3D") image correction in optical coherence tomography using a computer readable medium having stored thereon executable instructions, that when executed by a processor of a computer, control the computer to perform the method comprising:
   calibrating a scanning system of an OCT imaging system by imaging a calibration target with known physical dimensions including deriving numerical correction factors that describe the nonlinearities of the scanning system;
   obtaining a 3D image of a subject with the OCT imaging system;
   segmenting of index interface refracting surfaces from a raw OCT image dataset from an OCT system;
   calculating normal vectors or partial derivatives of a curvature at a refracting surface to obtain a refracted image voxel;
   iteratively computing a new position of each desired refracted image voxel;
   interpolating of new refracted corrected voxel positions to an even sampling grid to provide corrected image data; and
   correcting voxel positions using the numerical correction factors derived during calibration.

28. The method according to claim 27, further comprising repeating the steps of calculating normal vectors or partial derivatives of a curvature at a refracting surface to obtain a refracted image voxel, iteratively computing a new position of each desired refracted image voxel, and interpolating of new refracted corrected voxel positions to an even sampling grid to provide corrected image data until all desired refracting surfaces have been evaluated enabling computation and resampling of all desired image voxels.

29. The method according to claim 27, wherein segmenting comprises identifying external and internal sample surfaces at which refraction occurs.

30. The method according to claim 29, wherein the sample surfaces comprise anterior and posterior surfaces of a cornea or a lens.

31. The method according to claim 29, wherein segmenting comprises identifying locations within the sample surfaces at which to correct the raw OCT image dataset for refraction and index variations.

32. The method according to claim 31, wherein the identified locations comprise positions being at least one of below the first refracting surface or between all segmented refracting surfaces.

33. The method according to claim 31, wherein the identified locations comprise selected sample positions at which it is known that corrected data is to be obtained in order to calculate clinical parameters.

34. The method according to claim 27, wherein calculating normal vectors or partial derivatives of the curvature at the refracting surface comprises calculating a normal vector at each point on the segmented refracting surface where an OCT sample arm light strikes a sample.

35. The method according to claim 27, wherein calculating normal vectors or partial derivatives of the curvature at the refracting surface is dependent upon a scan pattern utilized to obtain the raw OCT dataset and upon a coordinate system desired for conducting further computations.

36. The method according to claim 35, wherein the coordinate system is at least one of a Cartesian coordinate system or a polar coordinate system.

37. The method according to claim 36, wherein the coordinate system is a Cartesian coordinate system, and wherein calculating normal vectors or partial derivatives of the curvature at the refracting surface comprises calculating the partial derivatives of the surface curvature in the x and y directions from surface normals.

38. The method according to claim 37, further comprising using a raster scan pattern oriented in the x or y direction to acquire data and calculating derivatives from one-dimensional polynomial functions fit using a least-squares fitting algorithm to each raster line in both orthogonal directions.

39. The method according to claim 37, further comprising using a radial scan pattern to acquire data and fitting surface points to a 3D Zernike polynomial model and subsequently calculating surface derivatives at every point by at least one of analytically or computationally.

40. The method according to claim 37, wherein calculating normal vectors or partial derivatives of the curvature at the refracting surface comprises using an equation of:

$$\overrightarrow{MC} \times (-\vec{n}) \cdot n_{air} = \overrightarrow{CC'} \times (-\vec{n}) \cdot n_c$$

where $\overrightarrow{MC}$ comprises a direction vector (a,b,c) of incident light; × represents a vector cross product; $\vec{n}$ is a unit surface normal vector of an arbitrary incident point C; $n_{air}$ is refractive index of air; $\overrightarrow{CC'}$ is unit vector of a refracted ray; and $n_c$ is refractive index of cornea.

41. The method according to claim 40, wherein the coordinate system is a Cartesian coordinate system, and wherein calculating normal vectors or partial derivatives of the curvature at the refracting surface comprises using equations of:

$$\begin{cases} z - z_0 = OPL/n_c \cdot \cos(\theta_{in} - \theta_r) \\ x = \dfrac{a*OPL}{n_c^2} + x_0 + \dfrac{\partial z_{EPI}}{\partial x}(c*OPL/n_c^2 - z + z_0) \\ y = \dfrac{b*OPL}{n_c^2} + y_0 + \dfrac{\partial z_{EPI}}{\partial y}(c*OPL/n_c^2 - z + z_0) \end{cases}$$

to convert each vector to its Cartesian form and solving the cross product of the equation: $\overrightarrow{MC} \times (-\vec{n}) \cdot n_{air} = \overrightarrow{CC'} \times (-\vec{n}) \cdot n_c$, assuming $n_{air}=1.0$, where $C(x_0, y_0, z_0)$ is an incident point on an epithelium; $\theta_{in}$ is an incidental angle; $\theta_r$ is a refraction angle; OPL is an optical path length in an OCT image; and z is a projection of OPL on the z-axis.

42. The method according to claim 27, wherein the step of interpolating of new refracted corrected voxel positions to an even sampling grid comprises re-sampling refracted corrected voxel reflectivity data back to an original Cartesian sampling grid.

43. The method according to claim 27, wherein the step of interpolating of new refracted corrected voxel positions to an even sampling grid comprises fitting corrected voxel data to a 3D Zernike polynomial model for re-sampling to a desired grid location.

44. The method according to claim 27, wherein the step of interpolating of new refracted corrected voxel positions to an even sampling grid comprises generating a set of corrected x, y, and z coordinates of the new corrected position of each desired image voxel beneath the refracting surface.

45. The method according to claim 44, wherein the step of interpolating of new refracted corrected voxel positions to an even sampling grid further comprises producing a set of interpolated corrected image brightness values as a function of x, y, and z coordinates of the even sampling grid.

46. A non-transitory computer readable medium having stored thereon executable instructions, that when executed by a processor of a computer, control the computer to perform steps comprising:
   calibrating a scanning system of an optical coherence tomography OCT imaging system by imaging a calibration target with known physical dimensions including deriving numerical correction factors that describe the nonlinearities of the scanning system;
   segmenting of index interface refracting surfaces from a raw OCT image dataset from an OCT system;
   correcting voxel positions for at least the segmented first refracting surface using the numerical correction factors derived during calibration;
   calculating a refracted image voxel position for at least a portion of voxels in the raw OCT image dataset; and
   computing clinical outputs from a corrected image data.

47. The non-transitory computer readable medium according to claim 46, comprising repeating the step of calculating a position of each desired refracted image voxel, and further comprising interpolating new refracted corrected voxel positions to an even sampling grid to provide corrected image data until all desired refracting surfaces have been evaluated enabling computation and resampling of all desired image voxels.

48. The non-transitory computer readable medium according to claim 46, wherein segmenting of index interface refracting surfaces from the raw OCT image dataset from an OCT system comprises identifying external and internal sample surfaces at which refraction occurs.

49. The non-transitory computer readable medium according to claim 48, wherein the sample surfaces comprise anterior and posterior surfaces of a cornea or a lens.

50. The non-transitory computer readable medium according to claim 48, wherein segmenting comprises identifying locations within the sample surfaces at which to correct the raw OCT image dataset for refraction and index variations.

51. The non-transitory computer readable medium according to claim 50, wherein the identified locations comprise positions being at least one of below the first refracting surface or between all segmented refracting surfaces.

52. The non-transitory computer readable medium according to claim 50, wherein the identified locations comprise selected sample positions at which it is known that corrected data is to be obtained in order to calculate clinical parameters.

53. The non-transitory computer readable medium according to claim 46, wherein calculating refracted image voxel positions comprises calculating a normal vector or partial derivatives of the curvature at each point on the segmented refracting surface where an OCT sample arm light strikes the sample.

54. The non-transitory computer readable medium according to claim 53, wherein calculating normal vectors or partial derivatives of the curvature at the refracting surface is dependent upon a scan pattern utilized to obtain the raw OCT image dataset and upon a coordinate system desired for conducting further computations.

55. The non-transitory computer readable medium according to claim 54, wherein the coordinate system is at least one of a Cartesian coordinate system or a polar coordinate system.

56. The non-transitory computer readable medium according to claim 55, wherein the coordinate system is a Cartesian coordinate system, and wherein calculating normal vectors or partial derivatives of the curvature at the refracting surface comprises calculating the partial derivatives of the surface curvature in the x and y directions from the surface normals.

57. The non-transitory computer readable medium according to claim 56, further comprising using a raster scan pattern oriented in the x or y direction to acquire data and calculating the derivatives from one-dimensional polynomial functions fit using a least-squares fitting algorithm to each raster line in both orthogonal directions.

58. The non-transitory computer readable medium according to claim 56, further comprising using a radial scan pattern to acquire data and fitting surface points to a 3D Zernike polynomial model and subsequently calculating surface derivatives at every point by at least one of analytically or computationally.

59. The non-transitory computer readable medium according to claim 53, wherein calculating normal vectors or partial derivatives of the curvature at the refracting surface comprises using an equation of:

$$\overrightarrow{MC} \times (-\vec{n}) \cdot n_{air} = \overrightarrow{CC'} \times (-\vec{n}) \cdot n_c$$

where $\overrightarrow{MC}$ comprises a direction vector (a,b,c) of incident light; × represents a vector cross product; $\vec{n}$ is a unit surface normal vector of an arbitrary incident point C; $n_{air}$ is refractive index of air; $\overrightarrow{CC'}$ is unit vector of a refracted ray; and $n_c$ is refractive index of subject and where calculations are applied after correcting the raw OCT image dataset for scanning non-linearities using the correction factors derived during calibration.

60. The non-transitory computer readable medium according to claim 59, wherein a Cartesian coordinate system is used, and wherein calculating normal vectors or partial derivatives of the curvature at the refracting surface comprises using equations of:

$$\begin{cases} z - z_0 = OPL/n_c \cdot \cos(\theta_{in} - \theta_r) \\ x = \dfrac{a * OPL}{n_c^2} + x_0 + \dfrac{\partial z_{EPI}}{\partial x}(c * OPL/n_c^2 - z + z_0) \\ y = \dfrac{b * OPL}{n_c^2} + y_0 + \dfrac{\partial z_{EPI}}{\partial y}(c * OPL/n_c^2 - z + z_0) \end{cases}$$

to convert each vector to its Cartesian form and solving a cross product of the equation: $\overrightarrow{MC} \times (-\vec{n}) \cdot n_{air} = \overrightarrow{CC'} \times (-\vec{n}) \cdot n_c$, assuming $n_{air} = 1.0$, where $C(x_0, y_0, z_0)$ is an incident point on an epithelium; $\theta_{in}$ is an incidental angle; $\theta_r$ is a refraction angle; OPL is an optical path length in an OCT image; and z is a projection of OPL on the z-axis and where calculations are applied after correcting the raw OCT image dataset for scanning non-linearities using the correction factors derived during calibration.

61. The non-transitory computer readable medium according to claim 46, wherein calculating the position of each desired refracted image voxel comprises generating the raw OCT image dataset comprising image brightness as a function of x, y, and z coordinates, a segmented image dataset of the index interface refracting surfaces comprising sets of the x, y, and z coordinates of the refracting surface, a set of surface normal vectors or partial derivatives of the curvature of the refractive surfaces, and a set of incident light direction vectors and where calculations are applied after correcting the raw OCT image dataset for scanning non-linearities using the correction factors derived during calibration.

62. The non-transitory computer readable medium according to claim 61, wherein calculating the position of each desired refracted image voxel comprises producing a set of corrected x, y, and z coordinates of the corrected position of each desired image voxel beneath the refracting surface and where calculations are applied after correcting the raw OCT image dataset for scanning non-linearities using the correction factors derived during calibration.

63. The non-transitory computer readable medium according to claim 47, wherein interpolating of new refracted corrected voxel positions to an even sampling grid comprises re-sampling refracted corrected voxel reflectivity data back to an original Cartesian sampling grid.

64. The non-transitory computer readable medium according to claim 47, wherein interpolating of new refracted corrected voxel positions to an even sampling grid comprises fitting corrected voxel data to a 3D Zernike polynomial model for re-sampling to a desired grid location.

65. The non-transitory computer readable medium according to claim 47, wherein interpolating of new refracted corrected voxel positions to an even sampling grid comprises generating a set of corrected x, y, and z coordinates of the new corrected position of each desired image voxel beneath the refracting surface.

66. The non-transitory computer readable medium according to claim 65, wherein interpolating of new refracted corrected voxel positions to an even sampling grid further comprises producing a set of interpolated corrected image brightness values as a function of x, y, and z coordinates of the even sampling grid and where calculations are applied after correcting the raw OCT image dataset for scanning non-linearities using the correction factors derived during calibration.

67. The non-transitory computer readable medium according to claim 46, wherein computing clinical outputs from corrected image data comprises generating a set of interpolated corrected image brightness values as a function of x, y, and z coordinates of the even sampling grid.

68. The non-transitory computer readable medium according to claim 67, wherein computing clinical outputs from corrected image data comprises producing a set of clinical output measures comprising numerical values, tables, graphs, images, and maps.

69. The non-transitory computer readable medium according to claim 46, wherein the raw OCT image dataset is of a cornea or a lens and wherein computing clinical outputs comprises one or more of generating thickness maps, generating elevation maps, generating curvature maps, computing wavefront aberrations, or calculating an angle between an iris and an endothelial surface.

70. The non-transitory computer readable medium according to claim 46, wherein the raw OCT image dataset is of a cornea and wherein computing clinical outputs from corrected image data comprises creating a corneal or lens thickness map by determining the normal distance between the two surfaces in the volumetric surface model via an analytical or numerical approach.

71. The non-transitory computer readable medium according to claim 70, wherein a Cartesian coordinate system is used to conduct further computations and a recursive half searching algorithm ("RHSA") numerical solution is used to solve for (x, y, z) that exists within a defined distance to the endothelial surface.

* * * * *